United States Patent
Cary

(10) Patent No.: US 9,207,236 B2
(45) Date of Patent: Dec. 8, 2015

(54) HIGHLY SIMPLIFIED LATERAL FLOW-BASED NUCLEIC ACID SAMPLE PREPARATION AND PASSIVE FLUID FLOW CONTROL

(75) Inventor: Robert B. Cary, Santa Fe, NM (US)

(73) Assignee: Los Alamos National Security, LLC, Los Alamos, NM (US)

( * ) Notice: Subject to any disclaimer, the term of this patent is extended or adjusted under 35 U.S.C. 154(b) by 397 days.

(21) Appl. No.: 12/940,973

(22) Filed: Nov. 5, 2010

(65) Prior Publication Data

US 2011/0117540 A1    May 19, 2011

Related U.S. Application Data

(63) Continuation-in-part of application No. PCT/US2009/002809, filed on May 5, 2009.

(60) Provisional application No. 61/126,645, filed on May 5, 2008.

(51) Int. Cl.
G01N 33/558 (2006.01)
G01N 1/40 (2006.01)

(52) U.S. Cl.
CPC .............. G01N 33/558 (2013.01); G01N 1/405 (2013.01)

(58) Field of Classification Search
None
See application file for complete search history.

(56) References Cited

U.S. PATENT DOCUMENTS

| | | |
|---|---|---|
| 3,667,607 A | 6/1972 | Brandt |
| 4,235,601 A | 11/1980 | Deutsch et al. |
| 4,960,691 A | 10/1990 | Gordon et al. |
| 5,354,538 A | 10/1994 | Bunce et al. |
| 5,578,467 A | 11/1996 | Schuster et al. |
| 5,618,494 A | 4/1997 | Bunce et al. |
| 5,716,819 A | 2/1998 | Chatterjee |
| 5,736,188 A | 4/1998 | Alcock et al. |
| 5,741,647 A | 4/1998 | Tam |
| 5,922,617 A | 7/1999 | Wang et al. |
| 6,007,999 A | 12/1999 | Clark |
| 6,037,127 A | 3/2000 | Ebersole et al. |
| 6,146,589 A | 11/2000 | Chandler |

(Continued)

FOREIGN PATENT DOCUMENTS

| | | |
|---|---|---|
| CN | 1254844 A | 5/2000 |
| CN | 1954214 A | 4/2007 |

(Continued)

OTHER PUBLICATIONS

"Microarray technology: An array of opportunities", Nature, vol. 416, Macmillan Magazines, Ltd., Apr. 25, 2002, 885-891.

(Continued)

*Primary Examiner* — Chris L Chin
(74) *Attorney, Agent, or Firm* — Philip D. Askenazy; Janeen C. Vilven-Doggett; Peacock Myers, P.C.

(57) ABSTRACT

Highly simplified lateral flow chromatographic nucleic acid sample preparation methods, devices, and integrated systems are provided for the efficient concentration of trace samples and the removal of nucleic acid amplification inhibitors. Methods for capturing and reducing inhibitors of nucleic acid amplification reactions, such as humic acid, using polyvinylpyrrolidone treated elements of the lateral flow device are also provided. Further provided are passive fluid control methods and systems for use in lateral flow assays.

17 Claims, 21 Drawing Sheets
(14 of 21 Drawing Sheet(s) Filed in Color)

(56) References Cited

U.S. PATENT DOCUMENTS

| | | | |
|---|---|---|---|
| 6,261,779 | B1 | 7/2001 | Barbera-Guillem et al. |
| 6,468,749 | B1 | 10/2002 | Ulanovsky et al. |
| 6,471,916 | B1 | 10/2002 | Noblett |
| 6,555,349 | B1 | 4/2003 | O'Donnell |
| 7,094,536 | B2 | 8/2006 | Kurn |
| 7,186,508 | B2 | 3/2007 | Lee et al. |
| 7,195,872 | B2 | 3/2007 | Agrawal et al. |
| 2002/0028475 | A1 | 3/2002 | Ligler et al. |
| 2002/0076825 | A1 | 6/2002 | Cheng et al. |
| 2002/0179445 | A1 | 12/2002 | Alajoki et al. |
| 2002/0192839 | A1 | 12/2002 | Mink et al. |
| 2003/0003514 | A1 | 1/2003 | Kovalenko |
| 2003/0008308 | A1 | 1/2003 | Enzelberger et al. |
| 2003/0044862 | A1 | 3/2003 | Giaccia et al. |
| 2003/0064364 | A1 | 4/2003 | Lockhart et al. |
| 2003/0100128 | A1 | 5/2003 | Kenjyou et al. |
| 2003/0170686 | A1 | 9/2003 | Hoet et al. |
| 2003/0190608 | A1 | 10/2003 | Blackburn |
| 2004/0058378 | A1 | 3/2004 | Kong et al. |
| 2004/0110167 | A1 | 6/2004 | Gerdes et al. |
| 2005/0014192 | A1 | 1/2005 | Kurn |
| 2005/0032730 | A1 | 2/2005 | Von Der Mulbe et al. |
| 2005/0079492 | A1 | 4/2005 | Burgess Jr. et al. |
| 2005/0112780 | A1 | 5/2005 | Song |
| 2005/0227275 | A1 | 10/2005 | Jung et al. |
| 2005/0243321 | A1 | 11/2005 | Cohen et al. |
| 2005/0250141 | A1 | 11/2005 | Lambert et al. |
| 2006/0024813 | A1 | 2/2006 | Warthoe |
| 2006/0041058 | A1 | 2/2006 | Yin et al. |
| 2006/0127886 | A1 | 6/2006 | Kaylor et al. |
| 2006/0154286 | A1 | 7/2006 | Kong et al. |
| 2006/0160078 | A1 | 7/2006 | Cardy et al. |
| 2006/0177873 | A1 | 8/2006 | Dowd |
| 2006/0239859 | A1* | 10/2006 | Ohman et al. .............. 422/100 |
| 2006/0246601 | A1 | 11/2006 | Song et al. |
| 2006/0286570 | A1 | 12/2006 | Rowlen et al. |
| 2007/0015166 | A1 | 1/2007 | Nilsen |
| 2007/0020768 | A1 | 1/2007 | Rundstrom et al. |
| 2008/0207892 | A1 | 8/2008 | Iwaki |
| 2008/0280285 | A1* | 11/2008 | Chen et al. ..................... 435/5 |
| 2009/0130719 | A1 | 5/2009 | Handique |
| 2010/0248273 | A1 | 9/2010 | Campbell et al. |

FOREIGN PATENT DOCUMENTS

| | | | |
|---|---|---|---|
| CN | 10140993 | | 4/2009 |
| EP | 0 805 215 | A2 | 5/1997 |
| EP | 1972938 | A1 | 9/2008 |
| GB | 2 261 284 | A | 5/1993 |
| JP | 2006-520190 | | 9/2006 |
| JP | 2007-503968 | | 3/2007 |
| JP | 2009100761 | | 5/2009 |
| WO | 97/03207 | | 1/1997 |
| WO | 00/29112 | | 5/2000 |
| WO | 2004/09055 | A1 | 10/2004 |
| WO | 2004/092342 | A2 | 10/2004 |
| WO | WO 2006/122311 | * | 11/2006 .............. F24D 9/00 |
| WO | 2007083388 | | 7/2007 |
| WO | 2009/103843 | A2 | 8/2009 |
| WO | 2009/137509 | A1 | 11/2009 |

OTHER PUBLICATIONS

Akane, Atsushi et al., "Identification of the Heme Compound Copurified with Deoxyribonucleic Acid (DNA) from Bloodstains, a Major Inhibitor of Polymerase Chain Reaction (PCR) Amplification1", Journal of Forensic Sciences, vol. 39, No. 2, ASTM Internationa, Mar. 1994, 362-372.

Albretsen, Catrine et al., "Optimal Conditions for Hybridization with Oligonucleotides: A Study with myc-Oncogene DNA Probes", Analytical Biochemistry, vol. 170, Academic Press, Inc., 1988, 193-202.

An, Lixin et al., "Characterization of a Thermostable UvrD Helicase and Its Participation in Helicase-dependent Amplification", The Journal of Biological Chemistry, vol. 280, No. 32, American Society for Biochemistry and Molecular Biology, Inc., Aug. 12, 2005, 28952-28958.

Andreotti, Peter E. et al., "Immunoassay of infectious agents", BioTechniques Euro Edition, vol. 35, No. 4, Oct. 2003, 850-859.

Ausbel, et al., "Current Protocols in Molecular Biology", John Wiley & Sons, Inc., 1992, 15.6.1-15.6.4.

Baeumner, Antje J. et al., "A rapid biosensor for viable B. anthracis spores", Anal. Bioanal. Chem., vol. 380, 2004, 15-23.

Baeumner, Antje J. et al., "A Universal Nucleic Acid Sequence Biosensor with Nanomolar Detection Limits", Analytical Chemistry, vol. 76, No. 4, American Chemical Society, Feb. 15, 2004, 888-894.

Baeumner, Antje J. et al., "Biosensor for Dengue Virus Detection: Sensitive, Rapid, and Serotype Specific", Analytical Chemistry, vol. 74, No. 6, American Chemical Society, Mar. 15, 2002, 1442-1448.

Baeumner, Antje J., "Biosensors for environmental pollutants and food contaminants", Anal Bioanal Chem, vol. 377, 2003, 434-445.

Barany, Francis, "The Ligase Chain Reaction in a PCR World", Genome Research, vol. 1, Cold Spring Harbor Laboratory Press, Aug. 1991, 5-16.

Berthelet, Marc et al., "Rapid, direct extraction of DNA from soild for PCR analysis using polyvinylpyrrolidone spin columns", FEMS Microbiology Letter, vol. 138, Federation of European Microbiological Societies, 1996, 17-22.

Biagini, Raymond E. et al., "Rapid, Sensitive, and Specific Lateral-Flow Immunochromatographic Device to Measure Anti-Anthrax Protective Antigen Immunoglobulin G in Serum and Whole Blood", Clinical and Vaccine Immunology, vol. 13, No. 5, May 2006, 541-546.

Blake, R. D. et al., "Thermodynamic effects of formamide on DNa stability", Nucleic Acids Research, vol. 24, No. 11, Oxford University Press, 1996, 2095-2103.

Boom, R. et al., "Rapid and Simple Method for Purification of Nucleic Acids", Journal of Clinical Microbiology, vol. 28, No. 3, American Society for Microbiology, Mar. 1990, 495-503.

Boom, R. et al., "Rapid Purification of Hepatitis B Virus DNA from Serum", Journal of Clinical Microbiology, vol. 29, No. 9, American Society for Microbiology, Sep. 1991, 1804-1811.

Braasch, Dwaine A. et al., "Locked nucleic acid (LNA): fine-tuning the recognition of DNa and RNA", Chemistry & Biology, vol. 8, Elsevier Science Ltd., 2001, 731-735.

Bright, Rick A. et al., "Incidence of adamantane resistance among influenza A (H3N2) viruses isolated worldwide from 1994 to 2005: a cause for concern", Lancet, vol. 366, Sep. 22, 2005, 1175-1181.

Brlansky, R. H. et al., "Colonization of the Sharpshooter Vectors, Oncometopia nigricans and Homalodisca coagulata, by Xylem-LOimited Bacteria", Phytopathology, vol. 73, No. 4, The American Phytopathological Society, 1983, 530.535.

Brlansky, R. H. et al., "Transmission of the Citrus Variegated Chlorosis Bacterium Xylella fastidiosa with the Sharpshooter Oncometopia nigricans", Plant Disease, vol. 86, No. 11, American Phytopathological Society, Nov. 2002, 1237-1239.

Buck, G. A. et al., "Design Strategies and Performance of Custom DNA Sequencing Primers", BioTechniques, vol. 27, No. 3, 1999, 528-536.

Buhro, William E. et al., "Semiconductor nanocrystals: Shapematters", Nature Materials, vol. 2, No. 3, Nature Publishing Group, Mar. 2003, 138-139.

Capaldi, Stephen et al., "Signal amplification through nucleotide extension and excision on a dendritic DNA platform", Nucleic Acids Research, vol. 28, No. 7, Oxford University Press, 2000, i-vii.

Carter, Darren J. et al., "Lateral flow microarrays: a novel platform for rapid nucleic acid detection based on miniaturized lateral flow chromatography", Nucleic Acids Research, vol. 35, No. 10, 2007, 1-11.

Caruthers, Jonathan M. et al., "Helicase structure and mechanism", Curr Opin Struc Biol, vol. 12, 2002, 123-133.

Chang, Chung J. et al., "Culture and Serological Detection of the Xylem-Limited Bacterium Causing Citrus Variegated Chlorosis and Its Identification as a Strain of Xylella fastidiosa", Current Microbiology, vol. 27, Springer-Verlag New York, Inc., 1993, 137-142.

(56) References Cited

OTHER PUBLICATIONS

Chanteau, Suzanne et al., "Early diagnosis of bubonic plague using F1 antigen capture ELISA assay and rapid immunogold dipstick", Int. J. Med. Microbiol., vol. 290, No. 3, Urgan & Fischer Verlag, 2000, 279-283.
Cheek, Brady J. et al., "Chemiluminescence Detection for Hybridization Assays on the Flow-Thru Chip, a Three-Dimensional Microchannel Biochip[", Analytical Chemistry, vol. 73, No. 24, American Chemical Society, Dec. 15, 2001, 5777-5783.
Chin, Curtis D. et al., "Lab-on-a-chip devices for global health: Past Studies and future opportunities", Lab Chip, vol. 7, The Royal Society of Chemistry, 2007, 41-57.
Ciapina, L. P. et al., "A nested-PCR assay for detection of Xylella fastidiosa in citrus plants and sharpshooter leafhoppers", Journal of Applied Microbiology, vol. 96, Society for Applied Microbiology, 2004, 546-551.
Cirino, Nick M. et al., "Multiplex diagnostic platforms for detection of biothreat agents", Expert Rev. Mol. Diagn., vol. 4, No. 6, Future Drugs, Ltd., 2004, 841-857.
Collins, Ruairi, "Purification and characterization of Thermus thermophilus UvrD", Extremophiles, vol. 7, 2003, 35-41.
Compton, J., "Nucleic acid sequence-based amplification", Nature, vol. 350, Nature Publishing Group, Mar. 7, 1991, 91-92.
Cook, Alan F. et al., "Synthesis and hybridization of a series of biotinylated oligonucleotides", Nucleic Acids Research, vol. 16, No. 9, IRL Press Limited, Oxford, England, 1988, 4077-4095.
Cubero, J. et al., "Genetic Relationship among Worldwide Strains of Xanthomonas Causing Canker in Citrus Species and Design of New Primers for Their Identification by PCR", Applied and Environmental Microbiology, vol. 68, No. 3, American Society for Microbiology, Mar. 2002, 1257-1264.
Cubero, J. et al., "Quantitative PCR Method for Diagnosis of Citrus Bacterial Canker", Applied and Environmental Microbiology, vol. 67, No. 6, American Society for Microbiology, Jun. 2001, 2849-2852.
Davis, Michael J. et al., "Pierce's Disease of Grapevines: Isolation of the Causal Bacterium", Science, vol. 199, Jan. 6, 1978, 775-778.
Dawson, Erica D. et al., "Identification of A/H5N1 Influenza Viruses Using a Single Gene Diagnostic Microarray", Anal. Chem., vol. 79, American Chemical Society, 2007, 378-384.
Day, Philip J. et al., "Immobilization of polynucleotides on magnetic particles", Biochem. J., vol. 278, 1991, 735-740.
De Jong, Menno D. et al., "Oseltamivir Resistance during Treatment of Influenza A (H5N1) Infection", New England Journal of Medicine, vol. 353, No. 25, Massachusetts Medical Society, Dec. 22, 2005, 2667-2672.
Deiman, Birgit et al., "Characteristics and Applications of Nucleic Acid Sequence-Based Amplification (NASBA)", Molecular Biotechnology, vol. 20, Humana Press, Inc., 2002, 163-179.
Dineva, Magda A. et al., "Simultaneous Visual Detection of Multiple Viral Amplicons by Dipstick Assay", Journal of Clinical Microbiology, vol. 43, No. 8, American Society for Microbiology, Aug. 2005, 4015-4021.
Dobkin, Carl et al., "RNA Replication: Required Itermediates and the Dissociation of Template, Product, and QB Replicase", Biochemistry, vol. 18, American Chemical Society, 1979, 2038-2044.
Dong, Feng et al., "A coupled complex of T4 DNA replication helicase (gp41) and polymerase (gp43) can perform rapid and processive DNA strand-displacement synthesis", Proc. Natl. Acad. Sci. USA, vol. 93, Dec. 1996, 14456-14461.
Duck, P. et al., "Probe Amplifier System Based on Chimeric Cycling Oligonucleotides", Biotechniques, vol. 9, No. 2, 1990, 142-148.
Easterday, W. R. et al., "Use of Single Nucleotide Polymorphisms in the plxR Gene for Specific Identification of Bacillus Anthracis", Journal of Clinical Microbiology, vol. 43, No. 4, American Society for Microbiology, Apr. 2005, 1995-1997.
Easterday, William R. et al., "Specific detection of Bacillus Anthracis using a TaqMan mismatch amplification mutation assay", BioTechniques, vol. 38, No. 5, 2005, 731-735.
Edwards, Katie A. et al., "Optimization of DNA-tagged dye-encapsulating liposomes for lateral-flow assays based on sandwich hybridization", Anal. Bioanal. Chem., vol. 386, 2006, 1335-1343.
Elliott, K. et al., "Use of laser microdissection greatly improves the recovery of DNA from sperm on microscope slides", Forensic Science International, vol. 137, No. 1, Elsevier Ireland Ltd., 2003, 28-36.
Fong, Whalley K. et al., "Rapid Solid-Phase Immunoassay for Detection of Methicillin-Resistant Staphylococcus aureus Using Cycling Probe Technology", Journal of Clinical Microbiology, vol. 38, No. 7, American Society for Microbiology, Jul. 2000, 2525-2529.
Fukuta, Shiro et al., "Development of immunocapture reverse transcription loop-mediated isothermal amplification for the detection of tomato spotted wilt virus from chrysanthemum", Journal of Virological Methods, vol. 121, No. 1, Elsevier B.V., 2004, 49-55.
Gani, Raymond et al., "Potential Impact of Antiviral Drug Use during Influenza Pandemic", Emerging Infectious Diseases, vol. 11, No. 9,, Sep. 2005, 1355-1362.
Gill, Peter et al., "An investigation of the rigor of interpretation rules for STRs derived from less than 100 pg of DNA", Forensic Science International, vol. 112, Elsevier Science Ireland Ltd., 2000, 17-40.
Gill, Peter, "Application of Low Copy Number DNA Profiling", Croatian Medical Journal, vol. 42, No. 3, 2001, 228-232.
Glynou, Kyriaki et al., "Oligonucleotide-Functionalized Gold Nanopartices as Probes in a Dry-Reagent Strip Biosensor for DNA Analysis by Hybridization", Analytical Chemistry, vol. 75, No. 16, American Chemical Society, Aug. 15, 2003, 4155-4160.
Goheen, A. C. et al., "Association of a Rickettsialike Organism with Pierce's Disease of Grapevines and Alfalfal Swarf and Heat Therapy of the Disease in Grapevines", Phytopathology, vol. 63, Mar. 1973, 341-345.
Grainge, Ian et al., "Biochemical analysis of components of the pre-replication complex of Archaeoglobus fulgidus", Nucleic Acids Research, vol. 31, No. 16, Oxford University Press, 2003, 4888-4898.
Groody, E. P., "Detection of Foodborne Pathogens Using DNA Probes and a Dipstick Format", Molecular Biotechnology, vol. 6, Humana Press, Inc., 1996, 323-327.
Guatelli, John C. et al., "Isothermal, in vitro amplification of nucleic acids by a multienzyme reaction modeled after retroviral replication", Proc. Natl. Acad. Sci. USA, vol. 87, Mar. 1990, 1874-1878.
Guo, Zhen et al., "Direct fluorescence analysis of genetic polymorphisms by hybridization with oligonucleotide arrays on glass supports", Nucleic Acids Research, vol. 22, No. 24, Oxford University Press, 1994, 5456-5465.
Harmon, Frank G. et al., "Biochemical Characterization of the DNA Helicase Activity of the Escherichia coli RecQ Helicase", The Journal of Biological Chemistry, vol. 276, No. 1, American Society for Biochemistry and Molecular Biology, Inc., 2001, 232-243.
Hartley, Harriet A. et al., "Biosensor for the specific detection of a single viable B. Anthracis spore", Anal. Bioanal. Chem., vol. 376, 2003, 319-327.
Hartung, J. S. et al., "Detection of Xanthomonas campestris pv. Citri by the Polymerase Chain Reaction Method", Applied and Environmental Microbiology, vol. 59, No. 4, American Society for Microbiology, Apr. 1993, 1143-1148.
Hartung, John S. et al., "Rapid and Sensitive Colorimetric Detection of Xanthomonas axonopodis pv. citri by Immunocapture and a Nested-Polymerase Chain Reaction Assay", Phytopathology, vol. 86, No. 1, American Phytopathological Society, 1996, 95-101.
Heller, M. J., "DNA microarray technology: devices, systems, and applications", Annu. Rev. Biomed. Eng., vol. 4, 2002, 129-153.
Hendson, Mavis et al., "Genetic Diversity of Pierce's Disease Strains and Other Pathotypes of Xylella Fastidiosa", Applied and Environmental Microbiology, vol. 67, No. 2, American Society for Microbiology, Feb. 2001, 895-903.
Hill, B. L. et al., "Acquisition and Retention of Xylella Fastidiosa by an Efficient Vector, Graphocephala atropunctata", Phytopathology, vol. 85, No. 2, American Phytopathological Society, 1997, 209-212.
Hill, B. L. et al., "Populations of Xylella fastidiosa in Plants Required for Transmission by an Efficient Vector", Phytopathology, vol. 87, No. 12, American Phytopathological Society, 1997, 1197-1201.
Hill, Karen K. et al., "Fluorescent Amplified Fragment Length Polymorphism Analysis of Bacillus anthracis, Bacillus cereus, and

(56) References Cited

OTHER PUBLICATIONS

Bacillus thuringiensis Isolates", Applied and Environmental Microbiology, vol. 70, No. 2, American Society for Microbiology, Feb. 2004, 1068-1080.

Hopkins, D. I., "Xylella Fastidiosa: Xylem-Limited Bacterial Pathogen of Plants", Ann. Rev. Phytopathol., vol. 27, Annual Reviews Inc., 1989, 271-290.

Huber, Martin et al., "Accessing Single Nucleotide Polymorphisms in Genomic DNA by Direct Multiplex Polymerase Chain Reaction Amplification on Oligonucleotide Microarrays", Analytical Biochemistry, vol. 303, Elsevier Science (USA), 2002, 25-33.

Huckle, David, "Point-of-care diagnostices: will the hurdles be overcome this time?", Expert Review of Medical Devices, vol. 3.4, 2006, 421-426.

Ilyushina, Natalia A. et al., "Detection of amantadine-resistant variants among avian influenza viruses isolated in North America and Asia", Virology, vol. 341, Elsevier, Inc., 2005, 102-106.

Jacobi, V. et al., "Development of a multiplex immunocapture RT-PCR assay for detection and differentiation of tomato and tobacco mosaic tobamoviruses", Journal of Virological Methods, vol. 74, Elsevier Science B.V., 1998, 167-178.

Jacobsen, Nana et al., "Direct isolation of poly(A)+ RNA from 4 M guanidine thiocyanate-lysed cell extracts using locked nucleic acidoligo(T) capture", Nucleic Acid Research, vol. 32, No. 7, Oxford University Press, 2004, 1031-1042.

Jobling, Mark A. et al., "Encoded Evidence: DNA in Forensic Analysis", Nature Reviews: Genetics, vol. 5, Oct. 2004, 739-751.

Kandimalla, Ekambar R. et al., "Design, biochemical, biophysical and biological properties of cooperative antisense oligonucleotides", Nucleic Acids Research, vol. 23, No. 17, Oxford University Press, 1995, 3578-3584.

Kaplan, Daniel L. et al., "DnaB from Thermus aquaticus Unwinds Forked Duplex DNA with an Asymmetric Tail Length Dependence", The Journal of Biological Chemistry, vol. 274, No. 11, American Society for Biochemistry and Molecular Biology, Inc., Mar. 12, 1999, 6889-6897.

Keohavong, Phouthone et al., "Fidelity of DNa polymerases in DNA amplification", Proc. Natl. Acad. Sci. USA, vol. 86, Dec. 1989, 9253-9257.

Kieleczawa, Jan et al., "DNA Sequencing by Primer Walking with Strings of Continguous Hexamers", Science, vol. 258, No. 5089, American Association for the Advancement of Science, Dec. 11, 1992, 1787-1791.

Kievits, Tim et al., "NASBA (TM) isothermal enzymatic in vitro nucleic acid amplification optimzed for the diagnosis of HIV-1 infection", Journal of Virological Methods, vol. 35, Elsevier Science Publishers B.V., 1991, 273-286.

Kilbourne, Edwin D. et al., "The total influenza vaccine failure of 1947 revisited: Major intrasubtypic antigenic change can explain failure of vaccine in a post-World War II epidemic", PNAS, vol. 99, No. 16, Aug. 6, 2002, 10748-10752.

Kimura, et al., "One-step immobilization ofr poly(dT)-modified DNA onto non-modified plastic substrates by UV irradiation for microarrays", Biochemical and Biophysical Research Communications, vol. 347, 2006, 477-484.

Koch, Walter H., "Technology Platforms for Pahrmacogenomic Diagnostic Assays", Nature Reviews Drug Discovery, vol. 3, Sep. 2004, 749-761.

Kohn, J., "An Immunochromatographic Technique", Immunology, vol. 15, 1968, 863-865.

Koonjul, Priyum K., "Inclusion of polyvinylpyrrolidone in the polymerase chain reaction reverses the inhibitory effects of polyphenolic contamination of RHNA", Nucleic Acids Research, vol. 27, No. 3, Oxford University Press, 1999, 915-916.

Kornberg, et al., DNA Replication, 2nd Edition, WH Freeman and Company, New York, 1992, 298-299; 356-365.

Kozwich, Diane et al., "Development of a Novel, Rapid Integrated Cryptosporidium Parvum Detection Assay", Applied and Environmental Microbiology, vol. 66, No. 7, American Society for Microbiology, Jul. 2000, 2711-2717.

Kwoh, D. Y. et al., "Transcription-based amplification system and detection of amplified human immunodeficiency virus type 1 with a bead-based sandwich hybridization format", Proc. Natl. Acad. Sci. USA, vol. 86, Feb. 1989, 117301177.

Landegren, Ulf et al., "A Ligase-Mediated Gene Detection Technique", Science, vol. 241, Aug. 26, 1988, 1077-1080.

Lane, Michael J. et al., "The thermodynamic advantage of DNA oligonucleotide 'stacking hybridization' reactions: energetics of a DNA nick", Nucleic Acids Research, vol. 25, No. 3, Oxford University Press, 1997, 611-616.

Leone, G. et al, "Direct detection of potato leafroll virus in potato tubers by immunocapture and the isothermal nuclic acid amplification method NASBA", Journal of Virological Methods, vol. 66, Elsevier Science B.V., 1997, 19-27.

Lim, Daniel V. et al., "Current and Developing Technologies for Monitoring Agents of Bioterrorism and Biowarfare", Clinical Microbiology Reviews, vol. 18, No. 4, American Society for Microbiology, Oct. 2005, 583-607.

Lockley, Andrew K. et al., "Colorimetric detection of immobilised PCR products generated on a solid support", Nucleic Acids Research, vol. 25, No. 6, Oxford University Press, 1997, 1313-1314.

Loens, K. et al., "Evaluation of NucliSens easyMAG for Automated Nucleic Acid Extraction from Various Clinical Specimens", Journal of Clinical Microbiology, vol. 45, No. 2, American Society for Microbiology, Feb. 2007, 421-425.

Lonnberg, Maria et al., "Chromatographic performance of a thin microporous bed of nitrocellulose", Journal of Chromatography B, vol. 763, Elsevier Science BV, 2001, 107-120.

Lowe, Mary et al., "Multiplexed, Particle-Based Detection of DNa Using Flow Cytometry with 3DNA Dendrimers for Signal Amplification", Cytometry Part A, vol. 60, No. 2, Wiley Intersciences, 2004, 135-144.

Mackay, I. M., "Real-time PCR in the microbiology laboratory", Clin Microbiol Infect., vol. 10, European Society of Clinical Microbiology and Infectious Diseases, 2004, 190-212.

Malek, Larry et al., "Nucleic acid sequence-based amplification (NASBA)", Protocols for Nucleic Acid Analysis by Nonradioactive Probes, ed. Peter G. Isaac, Humana Press, Totowa, New Jersey, 1994, 253-260.

Michalet, Xavier et al., "Properties of Fluorescent Semiconductor Nanocrystals and their Application to Biological Labeling", Single Mol., vol. 2, No. 4, Wiley-VCH Verlag Berlin GmbH, 2001, 261-276.

Miyoshi, Daisuke et al., "Molecular Crowding Regulates the Structural Switch of the DNA G-Quadruplex", Biochemistry, vol. 41, American Chemical Society, Nov. 20, 2002, 15017-15024.

Monteiro, Lurdes et al., "Complex Polysaccharides as PCR Inhibitors in Feces: Helicdobacter pylori Model", Journal of Clinical Microbiology, vol. 35, No. 4, American Society for Microbiology, Apr. 1997, 995-998.

Mumford, R. A. et al., "Rapid single-tube immunocapture RT-PCT for the detection of two yam potyviruses", Journal of Virological Methods, vol. 69, Elsevier Science B.V., 1997, 73-79.

Nicholson, Karl G. et al., "Influenza", The Lancet, vol. 362, Nov. 22, 2003, 1733-1745.

O'Meara, Deirdre et al., "Capture of Single-Stranded DNa Assisted by Oligonucleotide Modules", Analytical Biochemistry, vol. 255, Academic Press, 1998, 195-203.

O'Meara, Deirdre et al., "Cooperative Oligonucleotides Mediating Direct Capture of Hepatitis C Virus RNa from Serum", Journal of Clinical Microbiology, vol. 36, No. 9, American Society for Microbiology, Sep. 1998, 2454-2459.

Palese, Peter et al., "Influenza vaccines: present and future", The Journal of Clinical Investigation, vol. 110, No. 1, Jul. 2002, 9-13.

Pannucci, James et al., "Virulence signatures: microarray-based approaches to discovery and analysis", Biosensors and Biolelectronics, vol. 20, Elsevier, B.V., 2004, 706-718.

Pastinen, Tomi et al., "A System for Specific, High-throughput Genotyping by Allele-specific Primer Extension on Microarrays", Genome Research, vol. 10, No. 7, Cold Spring Harbor Laboratory Press, 2000, 1031-1042.

Pemov, A. et al., "DNA analysis with multiplex microarray-enhanced PCR", Nucleic Acid Research, vol. 33, No. 2, Oxford University Press, 2005, 1-9.

(56) References Cited

OTHER PUBLICATIONS

Petrik, J., "Diagnostic applications of microarrays", Transfusion Medicine, vol. 16, Blackwell Publishing, Ltd., 2006, 233-247.
Peytavi, Regos et al., "Microfluidic Device for Rapid (<15 min) Automated Microarray Hybridization", Clinical Chemistry, vol. 51, No. 19, 2005, 1836-1844.
Piepenburg, Olaf et al., "DNA Detection Using Recombination Proteins", PLoS Biology, vol. 4, No. 7, Jul. 2006, 1115-1121.
Pooler, M. R. et al., "Detection of Xylella fastidiosa in potential insect vectors by immunomagnetic separation and nested polymerase chain reaction", Letters in Applied Microbiology, vol. 25, Society for Applied Bacteriology, 1997, 1230126.
Pooler, Margaret R. et al., "Specifric PCR Detection and Identification of Xylella fastidiosa Strains Causing Citrus Variegated Chlorosis", Current Microbiology, vol. 31, Springer-Verlag New York, Inc., 1995, 377-381.
Pristoupil, T. I. , "Microchromatography and Microelectrophoresis on Nitrocellulose Membranes", Chromatographic Reviews, vol. 12, Elsevier Publishing Company, Amsterdam, Netherlands, 1970, 109-125.
Purcell, A. H. et al., "Fate of Pierce's Disease Strains of Xylella fastidiosa in Common Riparian Plants in Californiat", Plant Disease, vol. 83, No. 9, American Phytopathological Society, 1999, 825-830.
Purcell, Alexander H. et al., "Pierce's Disease Bacterium: Mechanism of Transmission by Leafhopper Vectors", Science, vol. 206, Nov. 16, 1979, 839-841.
Reinhartz, Avraham et al., "A novel rapid hybridization technique: paper chromatography hybridization assay (PACHA)", Gene, vol. 136, Elsevier Science Publishers B.V., 1993, 221-226.
Rodriguez, Jorge L. et al., "Detection and Diversity Assessment of Xylella fastidiosa in Field-Collected Plant and Insect Samples by Using 16S rRNA and gyrB Sequences", Applied and Environmental Microbiology, vol. 69, No. 1, American Society for Microbiology, Jul. 2003, 4249-4255.
Romero, Alicia et al., "Amplification and cloning of a long RNA virus genome using immunocapture-long RT-PCR", Journal of Virological Methods, vol. 66, No. 1, Elsevier Science B.V., 1997, 159-163.
Roper, Michael G. et al., "Advances in Polymerase Chain Reaction on Microfluidic Chips", Analytical Chemistry, vol. 77, No. 12, American Chemical Society, 2005, 3887-3894.
Rouse, Richard et al., "Microarray technology—an intellectual property retrospective", Pharmacogenomics, vol. 4, No. 5, Ashley Publications Ltd., 2003, 1462-2416.
Rule, Geoffrey S. et al., "Rapid method for visual identification of specific DNA sequences based on DNA-tagged liposomes", Clinical Chemistry, vol. 42, No. 8, 1996, 1206-1209.
Saiki, Randall K. et al., "Primer-Directed Enzymatic Amplification of DNA with a Thermostable DNA Poymerase", Science, vol. 239, Jan. 29, 1988, 487-491.
Sambrook, et al., Molecular Cloning: A Laboratory Manual, 3rd Edition, Cold Spring Harbor Laboratory Press, Cold Spring Harbor, New York, 2001, 9.47-9.55.
Schildkraut, Carl et al., "Dependence of the Melting Temperature of DNA on Salt Concentration", Biopolymers, vol. 3, 1965, 195-208.
Schwab, K. J. et al., "Immunoaffinity concentration and purification of waterborne enteric viruses for detection by reverse transcriptase PCR", 1996, 2086-2094.
Singh, Sanjay K. et al., "LNA (locked nucleic acids): synthesis and high-affinity nucleic acid recognition", Chem. Commun., vol. 4, 1998, 455-456.
Spiro, Alexander et al., "A Bead-Based Method for Multiplexed Identification and Quantitation of DNA Squences Using Flow Cytometry", Applied and Environmental Microbiology, vol. 66, No. 10, American Society for Microbiology, Oct. 2000, 4258-4265.
Stears, Robin L. et al., "A novel, sensitive detection system for high-density microarrays using dendrimer technology", Physiol. Genomics, vol. 3, American Physiological Society, 2000, 93-99.
Sterne, Max , "The use of Anthrax Vaccines Prepared from Avirulent (Uncapsulated) Variants of Bacillus anthracis", Onderstepoort Journal of Veterinary Science and Animal Industry, vol. 13, No. 2, Government Printer, Pretoria, Union of South Africa, Oct. 1939, 307-312.
Stiver, Grant , "The treatment of influenza with antiviral drugs", CMAJ, vol. 168, No. 1, Canadian Medical Association, Jan. 7, 2003, 49-57.
Sunen, Ester et al., "Recovery and detection of enterovirus, hepatits A virus and Norwalk virus in hardshell clams (Mercenaria mercenaria) by RT-PCT methods", Journal of Virological Methods, vol. 77, 1999, 179-187.
Tennikova, Tatiana B. et al., "An Introduction to Monolithic Disks as Stationary Phases for High Performance Biochromatography", J. High Resol. Chromatogr., vol. 23, No. 1, Wiley-VCH Verlag GmbH, 2000, 27-38.
Tennikova, Tatiana B. et al., "High-performance membrane chromatography: highly efficient separation method for proteins in ion-exchange, hydrophobic interaction and reversed-phase models", Journal of Chromatography, vol. 646, Elsevier Science Publishers B.V., 1993, 279-288.
Thommes, J. et al., "Membrane Chromatography—An Integrative Concept in the Downstream Processing of Proteins", Biotechnol. Prog. vol. 11, American Chemical Society and American Institute of Chemical Engineers, 1995, 357-367.
Tsai, Yu-Li et al., "Rapid Method for Separation of Bacterial DNA from Humic Substances in Sediments for Polymerase Chain Reaction", Applied and Environmental Microbiology, vol. 58, No. 7, American Society for Microbiology, Jul. 1992, 2292-2295.
Van Ness, Jeffrey et al., "Isothermal reactions for the amplification of oligonucleotides", PNAS, vol. 100, No. 8, Apr. 15, 2003, 4504-4509.
Vincent, Myriam et al., "Helicase-dependent isothermal DNa amplification", EMBO Reports, vol. 5, No. 8, European Molecular Biology Organization, 2004, 795-800.
Wahlestedt, Claes et al., "Potent and nontoxic antisense oligonucleotides containing locked nucleic acids", PNAS, vol. 97, No. 10, May 9, 2000, 5633-5638.
Walker, G. T. et al., "Isothermal in vitro amplification of DNA by a restriction enzyme/DNA apolymerase system", Proc. Natl. Acad. Sci. USA, vol. 89, Jan. 1992, 392-396.
Walker, G. T. et al., "Strand displacement amplification-an isothermal, in vitro DNA amplification technique", Nucleic Acid Research, vol. 20, No. 7, Oxford University Press, 1992, 1691-1696.
Webby, R. J. et al., "Are we ready for pandemic influenza?", Science, vol. 302, Nov. 28, 2003, 1519-1522.
Webster, Robert G. et al, "Potential Impact of Antiviral Drug Use during Influenza Pandemic", American Scientist, vol. 91, 2003, 122-129.
Wei, Cheng-Wey et al., "Using a microfluidic device for 1 ul DNA micrarray hybridization in 500 s", Nucleic Acids Research, vol. 33, No. 8, Oxford University Press, 2005, 1-11.
Wells, John M. et al., "Isolation, Culture, and Pathogenicity of the Bacterium Causing Phony Disease of Peach", Phytopathology, vol. 73, No. 6, American Phytopathological Society, 1983, 859-862.
Wetzel, T. et al., "A highly sensitive immunocapture polymerase chain reaction method for plum pox potyvirus detection", Journal of Virological Methods, vol. 39, Elsevier Science Publishers B.V., Jul. 1992, 27-37.
Wickenheiser, Ray A. , "Trace DNA: A Review, Discussion of Theory, and Application of the Transfer of Trace Quantities of DNA Through Skin Contact", J Forensic Sci, vol. 137, No. 1, ASTM Int'l, 2002, 442-450.
Wilson, I G. , "Inhibition and Facilitation of Nucleic Acid Amplification", Applied and Environmental Microbiology, vol. 63, No. 10, 1997, 3741-3751.
Yang, Samuel et al., "PCR-based diagnositcs for infectious diseases: uses, limitations, and future applications in acute-care settings", The Lancet Infectious Diseases, vol. 4, Jun. 2004, 337-348.
Young, Charles C. et al., "Polyvinylpyrrolidone-Agarose Gel Electrophoresis Purification of Polymerase Chain Reaction-Amplifiable DNA from Soils", Applied and Environmental Microbiology, vol. 59, No. 6, American Society for Microbiology, Jun. 1993, 1972-1974.
Zaytseva, Natalya V. et al., "Multi-analyte single-membrance biosensor for the serotype-specific detection of Dengue virus", Anal. Bioanal. Chem., vol. 380, 2004, 46-53.

(56) References Cited

OTHER PUBLICATIONS

Zijlmans, H.J.M.A.A. et al., "Detection of Cell and Tissue Surface Antigens Using Up-Converting Phosphors: A New Reporter Technology", Analytical Biochemistry, vol. 267, Academic Press, 1999, 30-36.

Zuiderwijk, Michel et al., "An amplication-free hybridization-based DNA assay to detect Streptococcus pneumoniae utilizing the upconvewrting phosphor technology", Clinical Biochemistry, vol. 36, The Canadian Society of Clinical Chemists, 2003, 401-403.

Aveyard, et al., "One step visual detection of PCR products with gold nanoparticles and a nucleic acid lateral flow (NALF) device", Chem. Commun., 2007, 4251-4253.

Carney, et al., "Present and future applications of gold in rapid assays", IVD Technology, Mar. 1, 2006, 1-8.

Corstjens, et al., "Use of Up-Converting Phosphor Reporters in Lateral-Flow Assays to Detect Specific Nucleic Acid Sequences: A Rapid, Sensitive DNA Test to Identify Human Papillomavirus Type 16 Infection", Clinical Chemistry, 2001, 1885-1893.

Goldmeyer, et al., "Development of a Novel One-Tube Isothermal Reverse Transcription Thermophilic Helicase-Dependent Amplification Platform for Rapid RNA Detection", Journal of Molecular Diagnostics, Nov. 2007, 639-644.

Aveyard, et al., "One Step Visual Detection of PCR Products with Gold Nanoparticles and a Nucleic Acid Lateral Flow (NALF) Device", Chemical Communications, 2007 (Electronic Supplementary Information).

Ralser, et al., "An efficient and economic enhancer mix for PCR", Biochemical and Biophysical Research Communications, 2006, 747-751.

Rao, et al., "Developing rapid, point-of-care, multiplex detection for use in lateral flow devices", Smart Medical and Biomedical Sensor Technology III, Proc. of SPIE, 2005.

Masny, et al., "Ligation mediated PCR performed at low denaturation temperatures—PCT melting profiles", Nucleic Acids Research, 2003, 1-6.

"Jikken Igaku Bessatsu Mokuteki De Eraberu PCR Jikken Protocol", Jan. 1, 2011, p. 50, Fig. 1B; p. 53, lines 1-12 (English translation of relevant passages attached).

\* cited by examiner

SEQUENCE LISTING

```
<160> NUMBER OF SEQ ID NOS: 14

<210> SEQ ID NO 1
<211> LENGTH: 52
<212> TYPE: DNA
<213> ORGANISM: Artificial Sequence
<220> FEATURE:
<223> OTHER INFORMATION: Description of Artificial Sequence:
      oligonucleotide

<400> SEQUENCE: 1
aattctaata cgactcacta tagggagaag gccatcgttg tgttcagcgt ta         52

<210> SEQ ID NO 2
<211> LENGTH: 41
<212> TYPE: DNA
```

```
<213> ORGANISM: Artificial Sequence
<220> FEATURE:
<223> OTHER INFORMATION: Description fo Artificial Sequence:
      oligonucleotide

<400> SEQUENCE: 2
gatgcaaggt cgcatatgag aactatcgct aaacatcgcc a                        41

<210> SEQ ID NO 3
<211> LENGTH: 20
<212> TYPE: DNA
<213> ORGANISM: Artificial Sequence
<220> FEATURE:
<223> OTHER INFORMATION: Description of Artificial Sequence:
      Oligonucleotide

<400> SEQUENCE: 3
ctgctcagaa ggttcgcctt                                                20

<210> SEQ ID NO 4
<211> LENGTH: 20
<212> TYPE: DNA
<213> ORGANISM: Artificial Sequence
<220> FEATURE:
<223> OTHER INFORMATION: Description of Artificial Sequence:
      oligonucleotide

<400> SEQUENCE: 4
ctgatttaga atgtgctgtg                                                20

<210> SEQ ID NO 5
<211> LENGTH: 20
<212> TYPE: DNA
<213> ORGANISM: Artificial Sequence
<220> FEATURE:
<223> OTHER INFORMATION: Description of Artificial Sequence:
      oligonucleotide

<400> SEQUENCE: 5
ttatgctata accacccagg                                                20

<210> SEQ ID NO 6
<211> LENGTH: 43
<212> TYPE: DNA
<213> ORGANISM: Artificial Sequence
<220> FEATURE:
<223> OTHER INFORMATION: Description of Artificial Sequence:
      oligonucleotide

<400> SEQUENCE: 6
ttatgctata accacccagg acgcgatgaa aaacgtctgg caa                      43

<210> SEQ ID NO 7
<211> LENGTH: 39
<212> TYPE: DNA
<213> ORGANISM: Artificial Sequence
<220> FEATURE:
<223> OTHER INFORMATION: detection probe derived from human thought
<220> FEATURE:
<221> NAME/KEY: misc_feature
<222> LOCATION: (3)..(3)
<223> OTHER INFORMATION: uracil-biotin
<220> FEATURE:
<221> NAME/KEY: misc_feature
<222> LOCATION: (7)..(7)
<223> OTHER INFORMATION: uracil-biotin
<220> FEATURE:
<221> NAME/KEY: misc_feature
<222> LOCATION: (12)..(12)
```

```
<223> OTHER INFORMATION: uracil-biotin

<400> SEQUENCE: 7
ttntttnttt tnttttttg atgcaaggtc gcatatgag                               39

<210> SEQ ID NO 8
<211> LENGTH: 51
<212> TYPE: DNA
<213> ORGANISM: Artificial Sequence
<220> FEATURE:
<223> OTHER INFORMATION: Description of Artificial Sequence:
      oligonucleotide

<400> SEQUENCE: 8
aattctaata cgactcacta tagggagaga aagcggacag aaacccgctg a                51

<210> SEQ ID NO 9
<211> LENGTH: 45
<212> TYPE: DNA
<213> ORGANISM: Artificial Sequence
<220> FEATURE:
<223> OTHER INFORMATION: Description of Artificial Sequence:
      oligonucleotide

<400> SEQUENCE: 9
gatgcaaggt cgcatatgag gacctgacaa aaatggagaa gatct                       45

<210> SEQ ID NO 10
<211> LENGTH: 47
<212> TYPE: DNA
<213> ORGANISM: Artificial Sequence
<220> FEATURE:
<223> OTHER INFORMATION: Description of Artificial Sequence:
      oligonucleotide

<400> SEQUENCE: 10
aattctaata cgactcacta tagggagatt ttcaacaatt gttctt                      47

<210> SEQ ID NO 11
<211> LENGTH: 40
<212> TYPE: DNA
<213> ORGANISM: Artificial Sequence
<220> FEATURE:
<223> OTHER INFORMATION: Description of Artificial Sequence:
      oligonucleotide

<400> SEQUENCE: 11
gatgcaaggt cgcatatgag tttgagttat ggcggacgtc                             40

<210> SEQ ID NO 12
<211> LENGTH: 40
<212> TYPE: DNA
<213> ORGANISM: Artificial Sequence
<220> FEATURE:
<223> OTHER INFORMATION: Description of Artificial Sequence:
      oligonucleotide

<400> SEQUENCE: 12
gatgcaaggt cgcatatgag ttatggtgaa cagtggatta                             40

<210> SEQ ID NO 13
<211> LENGTH: 45
<212> TYPE: DNA
<213> ORGANISM: Artificial Sequence
<220> FEATURE:
<223> OTHER INFORMATION: Description fo Artificial Sequence:
      oligonucleotide
```

```
<400> SEQUENCE: 13
aattctaata cgactcacta tagggggaaac aaatgcttag ggatt            45

<210> SEQ ID NO 14
<211> LENGTH: 22
<212> TYPE: DNA
<213> ORGANISM: Artificial Sequence
<220> FEATURE:
<223> OTHER INFORMATION: Description of Artificial Sequence:
      oligonucleotide
<220> FEATURE:
<221> NAME/KEY: misc_feature
<222> LOCATION: (15)..(15)
<223> OTHER INFORMATION: ideoxy uracil
<220> FEATURE:
<221> NAME/KEY: misc_feature
<222> LOCATION: (21)..(21)
<223> OTHER INFORMATION: ideoxy uracil

<400> SEQUENCE: 14
cataacgata ccacngaccc nc                                     22
```

HIGHLY SIMPLIFIED LATERAL FLOW-BASED NUCLEIC ACID SAMPLE PREPARATION AND PASSIVE FLUID FLOW CONTROL

CROSS-REFERENCE TO RELATED APPLICATIONS

This application is a continuation-in-part application of PCT International Application Number PCT/US2009/002809, filed on May 5, 2009, entitled "HIGHLY SIMPLIFIED LATERAL FLOW-BASED NUCLEIC ACID SAMPLE PREPARATION AND PASSIVE FLUID FLOW CONTROL", which application claims priority to and the benefit of the filing of U.S. Provisional Application No. 61/126,645, filed May 5, 2008, and the specifications and claims thereof, as well as the entire disclosures of all references, applications, patents, and publications cited therein, are incorporated herein by reference.

REFERENCE TO A SEQUENCE LISTING, A TABLE, OR COMPUTER PROGRAM

Applicant hereby submits a computer readable sequence listing as a text file titled "012111_v2_ST25.txt" and created Jan. 21, 2011.

STATEMENT AS TO RIGHTS TO INVENTIONS MADE UNDER FEDERALLY SPONSORED RESEARCH OR DEVELOPMENT

This invention was made with government support under Contract No. DE-AC52-06NA25396, awarded by the United States Department of Energy. The government has certain rights in this invention.

BACKGROUND OF THE INVENTION

The diverse nature of biological sample matrices present a need for robust yet general front-end sample processing methods that enable the collection of trace analytes even when present in complex mixtures of non-probative sample constituents. These challenges are often compounded by the presence of materials confounding to effective immunological or molecular analytical techniques. For example, samples derived from human tissue are likely to contain complex polysaccharides, hemoglobin, iron and other substances known to be inhibitory to DNA polymerases employed for polymerase chain reaction (PCR). Similarly, environmental samples or trace samples contaminated with environmental constituents, such as soil or plant material, can also contain organic materials, such as humic acids, that are strongly inhibitory to PCR and other enzymatic reactions critical to thorough nucleic acid analysis.

Although reliable nucleic acid isolation methods applicable to diverse biological samples have been reported for both DNA and RNA, such methods are labor intensive, dependent upon laboratory instrumentation and require hours to complete resulting in limited sample throughput and significant sample backlogs. Down-stream enzymatic manipulations, such as polymerase chain reaction (PCR), can be adversely impacted by the presence of matrix constituents inhibitory to enzymatic activity rendering reliable sample preparation indispensable. Hemoglobin, iron and complex polysaccharides are commonly encountered in biological samples while additional inhibitory compounds such as humic acids often accompany environmentally collected samples containing soil, plant material or decaying mater. Additionally, the trace nature of many analytes in diagnostic and forensic samples as well as the abundance of closely related but non-probative constituents contribute significantly to analytical challenges.

Lateral flow immuno-chromatography is well established and has been used for the detection of proteins and small molecules for many years. Indeed, immuno-capture during lateral flow is the basis for rapid hand-held immuno-assays that have found widespread use in the point-of-care (e.g. group A Streptococcal antigen) and in the home (e.g. pregnancy tests). While these assays make use of immuno-capture during lateral flow as a detection end-point, we propose the use of the same principle as a means of attaining rapid and efficient immuno-capture as a first step in a sample preparation strategy designed to enable the recovery of scarce targets (cells, viruses, spores) from mixed samples. Once captured in the stationary phase, these targets can then be subjected to further processing for nucleic acid isolation or collected for other analyses.

Nucleic acid-based assays for pathogen detection and identification offer sensitivity, specificity and resolution. These characteristics render nucleic acid analysis a powerful diagnostic and forensic technique. Nonetheless, many technologies for nucleic acid preparation have focused on isolation from relatively abundant samples such as clinical blood specimens. Many applications, however, often must address the need to isolate and identify trace constituents in complex mixed samples of diverse origin. In contrast to DNA-based assays, immunoassays have found widespread acceptance in low cost, easily used formats, perhaps most notable of which is the chromatographic lateral flow immunoassay. Lateral flow assays, also known as hand-held assays or dipstick assays, are used for a broad range of applications where rapid antigen detection is required in an easily used, low cost format. Lateral flow immunoassays have been successfully employed for pathogen identification, diagnostics, and environmental and agriculture surveillance. Several chromatographic lateral flow assays have been described for the detection of nucleic acid sequences using a variety of detection techniques. Early work made use of cumbersome enzymatic detection strategies that relied on time consuming manipulations of dipsticks following introduction of the sample and detection schemes poorly suited for multiplexed applications.

More recently described, the Lateral Flow Microarray (LFM) is a miniaturized lateral flow-based method for multiplexed nucleic acid detection (Carter, D. J. and R. B. Cary, *Lateral flow microarrays: a novel platform for rapid nucleic acid detection based on miniaturized lateral flow chromatography*. Nucleic Acids Res, 2007. 35(10): p. e74). The approach makes use of DNA microarray-like patterning of a small lateral flow chromatography strip allowing multiple nucleic acid sequences to be detected in a single assay. The reduced surface area of the device confers several advantages over traditional lateral flow device form factors. Sample volumes are reduced to 10 µL resulting in reduced reagent consumption as well as reduced sample transport times. Moreover, hybridization times exhibited by the lateral flow microarray (LFM) are significantly reduced compared to standard glass substrate microarrays, which typically are allowed to hybridize with sample for several hours, as well as more complex microarray implementations that make use of microfluidic systems to facilitate more rapid hybridization. The convective fluid movement through the lateral flow substrate as well as the open-ended pores of the membrane substrates employed result in superior chromatography performance compared to bead-based column chromatography.

These factors result in hybridization-based detection of <250 amol of analyte in 2 minutes. LFM is further described in U.S. patent application Ser. No. 11/894,910 and PCT International Application No. PCT/US2007/018537.

The LFM platform has been used to develop a rapid assay for *Bacillus anthracis*, the causative agent of anthrax, and has been shown to detect RNA from as few as 2-3 *B. anthracis* cells when present in a complex nucleic acid background consisting of 1 µg of total human RNA. The reported LFM approach made use of standard laboratory methods for RNA isolation and an isothermal RNA amplification scheme known as nucleic acid sequence based amplification (NASBA). Perhaps most significantly, the miniaturization of lateral flow exemplified by the LFM offers a physical configuration amenable to integration with fluidic or microfluidic systems for sample preparation support.

Integration of LFM-based protein and nucleic acid detection with simplified sample processing methods would offer several potential advantages for processing and screening of a broad range of sample types, and is desirable. Similarly, more robust sample preparation methods applicable to trace and/or dilute analytes would greatly facilitate nucleic acid amplification and detection in point of care and field deployed assays.

SUMMARY OF THE INVENTION

Embodiments of the present invention provide highly simplified lateral flow chromatographic nucleic acid sample preparation methods, devices, and integrated systems for the efficient concentration of trace samples and the removal of nucleic acid amplification inhibitors. The embodiments preferably make use of LFM technology and passive fluid flow control systems, enabling a combination of (a) rapid immuno-affinity capture of analytes, such as eukaryotic and prokaryotic cells, viruses and plant cells and material, and (b) hybridization-based affinity capture of specific DNA or RNA sequences to be concentrated and washed free of contaminating proteins and other matrix derived constituents after cell/virus lysis. The embodiments also preferably provide means for removing inhibitors of nucleic acid amplification reactions (i.e., PCR) within the context of a lateral flow device.

Embodiments of the present invention also provide lateral flow structures for passively controlling the flow of different and multiple solutions used in and the reaction sequences of a lateral flow assay. In one embodiment, at least the sample receiving zone of the LFSP device comprises a geometrically-defined absorbent material capable of supporting fluid wicking and the passive control of at least one fluid flow therein, such as nitrocellulose. In one embodiment, the invention provides a device comprising a lateral flow matrix which defines a flow path and which comprises a geometrically-defined absorbent material capable of supporting fluid wicking and the passive control of at least one fluid flow therein. In other non-limiting embodiments described herein, a geometrically-defined nitrocellulose strip has a configuration as shown in FIG. 5, 6, 7, 8, 9 or 14A.

The devices and systems of the invention are preferably easily fabricated and preferably use lateral capillary flow chromatographic substrates as a support for efficient low volume affinity purification of nucleic acids from biological samples. Sample preparation preferably enables highly efficient capture of trace analytes at spatially defined regions in a lateral flow sample preparation (LFSP) device. This results in a high local concentration of target analyte immobilized on the substrate, thus greatly facilitating extensive washing and additional manipulations including amplification with no user intervention or additional sample handling. These features, together with their compatibility with established molecular analytical techniques such as real-time PCR, MLVA, genotyping and other nucleic acid-based methods, render lateral flow sample concentration and processing an attractive means of obtaining suitable nucleic acids for environmental surveillance, disease diagnostics and bioforensic investigations.

In one embodiment, a LFSP device comprises a lateral flow matrix which defines a flow path and which comprises in series the following elements: (a) a sample receiving zone for receiving an aliquot of a fluid sample; and (b) an immuno-capture zone in lateral flow contact with said sample receiving zone, which contains immobilized antibody reactive with a ligand present on a biological particle or cell of interest. Another embodiment further comprises, in series: (c) a lysis zone, in lateral flow contact with said immuno-capture zone, wherein lysis of the biological particle or cell of interest is achieved, thereby liberating nucleic acid therefrom. In still another embodiment, a LFSP device further comprises, in series: (d) one or more assay zones, in lateral flow contact with the lysis zone, which together form the nucleic acid and labeling constituents for a sandwich nucleic acid hybridization assay. In yet another embodiment, a LFSP device further comprises a nucleic acid amplification zone downstream of and in lateral flow contact with the lysis zone, and upstream and in lateral flow contact with the assay zone(s). This aspect of the invention is further described by way of the Examples disclosed herein.

Embodiments of LFSP devices of the invention may also incorporate the invention's methods for capturing and reducing inhibitors of nucleic acid amplification reactions, such as humic acid, using polyvinylpyrrolidone treated elements of the lateral flow device. Thus, referring to the above embodiments, a further embodiment of a LFSP device further comprises a pre-treatment zone comprising polyvinylpyrrolidone, in lateral flow contact with the element or elements of the device to which it is adjacent. For example, a treatment zone may be placed upstream of and in lateral flow contact with the immuno-capture zone, and downstream and in lateral flow contact with the sample zone. In related embodiments, substances other then or in addition to polyvinylpyrrolidone may be incorporated into the pre-treatment zone in order to capture or reduce unwanted inhibitors or other contaminants from the sample matrix prior to amplification and/or assay. This aspect of the invention is described further in the Examples disclosed herein.

LFSP devices of the invention may also incorporate passive fluid control methods and systems. Briefly, passive solution or buffer flow control may be achieved by cutting lateral flow membranes (e.g., nitrocellulose membranes) or other bibulous material, such as chromatography paper capable of supporting capillary flow/fluid wicking, into distinct geometries, such that individual flow paths, of varying lengths and/or widths, are defined for each of the buffers to be employed in an assay conducted using the device, yet are integrated within a single membrane. This aspect of the invention is described further in the Examples disclosed herein.

LFSP devices of the invention may be used in any LF format, but may be particularly suited to use with LFM methods, devices and systems. Fully integrated, sample-to-answer assay devices comprising LFSP integrated with LFM are envisioned.

An embodiment of the present invention is also a method for measuring an amount of a target, the method comprising the steps of disposing a plurality of biological particles comprising one or more targets in a sample receiving zone; lysing the particles; and binding the targets to a first ligand in a capture zone in lateral flow connection with the sample receiving zone, thereby increasing a concentration of the target relative to other constituents in the particles. The particles are preferably selected from the group consisting of cells, viruses, and bacteria. The method preferably further comprises removing the other constituents from the capture zone. The method optionally further comprises increasing a concentration of the particles prior to the lysing step by reacting a second ligand with the surface of the particle. The second ligand optionally comprises an antibody or a carbohydrate. The binding step optionally comprises binding DNA with silica, binding RNA with silica, or providing a functionalized substrate for anion or cation exchange mediated enrichment of nucleic acids, proteins, or small molecules. The targets optionally comprise nucleic acids, in which case the method preferably further comprises adding a lysate such as a guanidinium lysate or a lysate generated with a chaotropic or kosmotropic salt or with a high ionic strength buffer and/or a wash buffer to a buffer exchanger that is in lateral flow contact with a nucleic acid affinity matrix; and directly purifying the nucleic acids.

Objects, other advantages and novel features, and further scope of applicability of the present invention will be set forth in part in the detailed description to follow, taken in conjunction with the accompanying drawing, and in part will become apparent to those skilled in the art upon examination of the following, or may be learned by practice of the invention. The objects and advantages of the invention may be realized and attained by means of the instrumentalities and combinations particularly pointed out in the appended claims.

BRIEF DESCRIPTION OF THE DRAWINGS

The patent or application file contains at least one drawing executed in color. Copies of this patent or patent application publication with color drawing(s) will be provided by the Office upon request and payment of the necessary fee.

The accompanying drawings, which are incorporated into and form a part of the specification, illustrate one or more embodiments of the present invention and, together with the description, serve to explain the principles of the invention. The drawings are only for the purpose of illustrating one or more preferred embodiments of the invention and are not to be construed as limiting the invention. In the drawings.

DETAILED DESCRIPTION OF THE INVENTION

Figure 1:
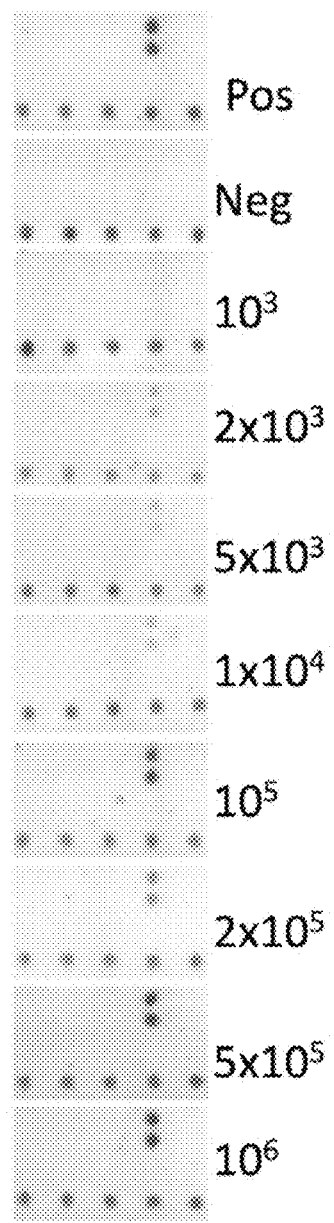
FIG. 1. Lateral flow microarrays (LFMs) were challenged with NASBA reactions programmed with crude lysate from the indicated number of *E. coli* cells. Positive hybridization controls mark each row of spots on the LFM (column of five spots on the left side of the LFMs) and a set of duplicate spots indicate positive detection of *E. coli* (second row from the bottom, right side). "Negative" is a no template control. "Positive" contains 6 ng of *E. coli* RNA isolated using a Qiagen RNeasy kit. As few as 2000 cells could be detected using a crude lysate prepared by heating cells in cells-to-cDNA buffer (Ambion). See Example 1, infra.

Unless otherwise defined, all terms of art, notations and other scientific terminology used herein are intended to have the meanings commonly understood by those of skill in the art to which this invention pertains, unless otherwise defined. In some cases, terms with commonly understood meanings are defined herein for clarity and/or for ready reference, and the inclusion of such definitions herein should not be construed to represent a substantial difference over what is generally understood in the art. The techniques and procedures described or referenced herein are generally well understood and commonly employed using conventional methodologies by those skilled in the art, such as, for example, the widely utilized molecular cloning methodologies described in Sambrook et al., Molecular Cloning: A Laboratory Manual 3rd. edition (2001) Cold Spring Harbor Laboratory Press, Cold Spring Harbor, N.Y. and Current Protocols in Molecular Biology (Ausbel et al., eds., John Wiley & Sons, Inc. 2001. As appropriate, procedures involving the use of commercially available kits and reagents are generally carried out in accordance with manufacturer defined protocols and/or parameters unless otherwise noted.

Lateral Flow Sample Preparation Methods and Systems

Embodiments of the invention provide highly simplified lateral flow chromatographic nucleic acid sample preparation methods, devices, and integrated systems for the efficient concentration of trace samples and the removal of nucleic acid amplification inhibitors. LFSP devices may consist of various elements and/or embodiments of the invention disclosed herein, including lateral flow immuno-capture of biological particles or cells, lysis directly within the lateral flow matrix, the various elements constituting a sandwich hybridization assay, passive fluid/buffer control systems, and pretreatment with compositions capable of sequestering or reducing the activity of nucleic acid amplification inhibitors.

For example, an embodiment of an LFSP device may comprises a sample receiving zone for receiving an aliquot of a fluid sample, together with an immuno-capture zone in lateral flow contact with said sample receiving zone, which contains immobilized antibody reactive with a ligand present on a biological particle or cell of interest. Such a device may be used to capture a biological particle or cell of interest, and may also contain means for lysing the particle or cell, and for amplifying the nucleic acid liberated therefrom. The device may be coupled to or integrated with a lateral flow assay, such as a sandwich hybridization nucleic acid assay. In certain embodiments, the LFSP devices are preferably coupled to or integrated with an LFM device or assay. LFM devices and assays are described in U.S. patent application Ser. No. 11/894,192.

Immuno-capture zones may be prepared, for example, as follows. A lateral flow substrate (i.e., nitrocellulose) is treated such that a ligand (e.g., antibody) is preferably immobilized to form an immuno-capture zone on the substrate. Specifically, antibody solutions are prepared in a physiological ionic strength buffer at a concentration found empirically to provide specific binding to the antigen (typically 0.01 mg/ml to 1 mg/ml). Antibody deposition onto a large pore nitrocellulose membrane can be accomplished by any of a number of means including but not limited to manual application, airbrush deposition, robotic fluid handling systems or similar methods that deposit controlled and reproducible volumes of ligand onto the substrate. Suitable substrates include HiFLow 135 (Millipore, Inc) and similar products available from a variety of commercial providers. Once deposited onto the substrate the ligand is preferably immobilized by drying (in the case of proteinaceous ligands) and/or by UV irradiation at a dose of 5000 microjoules (in the case of nucleic acid/LNA immobilization).

The lateral flow immuno-capture aspect of the invention preferably provides the capacity to concentrate target analytes from a wide range of dilute sample volumes. Once immobilized at the device's capture zone, the targets may be detected as well as subsequently washed, lysed and any liberated nucleic acids amplified. Incorporating multiple capture zones, each carrying ligands to different analytes, would enable the separation and collection of multiple sample constituents of interest for subsequent on- or off-device analyses. The multiplex capacity of this approach would allow multiple proteinaceous and nucleic acid analytes to be collected (and if desired detected) rapidly with minimal user intervention, requiring less than 2 minutes to obtain immuno-assay results and less than 60 minutes to obtain sensitive sequence specific nucleic acid amplification and detection.

In a simplified sample preparation scheme, based upon immuno-capture and subsequent chemical and/or heat-mediated lysis, removal of potential enzyme inhibitors and the impact of residual sample materials on amplification efficiency are preferably performed. Though crude cell lysate appropriately prepared can be used for NASBA (see Example 1, infra), applicant hypothesized that improved sensitivity could be achieved through the use of methods devised to further reduce cellular and matrix contaminants while simultaneously concentrating analyte particles from a complex mixture by means of immuno-affinity capture. LFSP methods and devices in accordance with the present invention are preferably capable of sequestering virus particles from a complex sample matrix, resulting in a cleansed viral sample that could be lysed to provide nucleic acids suitable for subsequent amplification without further purification. This aspect of the invention is described in more detail in Example 2, infra, wherein TMV particles were sequestered from crude macerated dried tobacco leaf by immuno-affinity chromatography within a nitrocellulose membrane context. The studies described in Example 2 demonstrate that lateral flow can be used to not only concentrate dilute analytes to a spatially defined capture zone but that regions of the device downstream of the capture zone are depleted with respect to the captured species. These data support the hypothesis that simple lateral flow immuno-assay methods can form the basis for a rapid and cost effective immuno-affinity purification system for separation and preparation of complex biological samples as well as the assertion that appropriately treated substrates can be used to deplete samples of unwanted constituents at downstream capture zones.

The samples utilized in the experiments described in Example 2 represent a very challenging matrix owing to the presence of complex polysaccharides, organic matter and other constituents strongly inhibitory to enzymatic manipulations, such as PCR and NASBA amplification, as well as potentially confounding non-probative nucleic acids (plant derived DNA and RNA). Therefore, the results described in Example 2 demonstrate the utility of a preceding lateral flow mediated immuno-capture step in the analysis of complex biological samples wherein the target analyte is a minority species and PCR and NASBA inhibitors are present that preclude direct amplification of the target without preparatory processing. Further, the results obtained in the experiments of Example 2 support the hypothesis that simple lateral flow immuno-assay methods can form the basis for a rapid and cost effective immuno-affinity purification system for separation and preparation of complex biological samples as well as the assertion that appropriately treated substrates can be used to deplete samples of unwanted constituents at downstream capture zones.

In some embodiments of the present invention, ligand capture (such as immuno-capture, wherein the ligand comprises one or more antibodies) concentrates the desired sample, such as a virus particle, on which lysis is subsequently performed and nucleic acids are amplified. In other embodiments, lysis may be performed without ligand capture, and the nucleic acids are bound directly to a binder.

In some embodiments of the present invention, neither centrifugation nor washing is required.

Passive LF Buffer Exchange Systems

Figure 7:
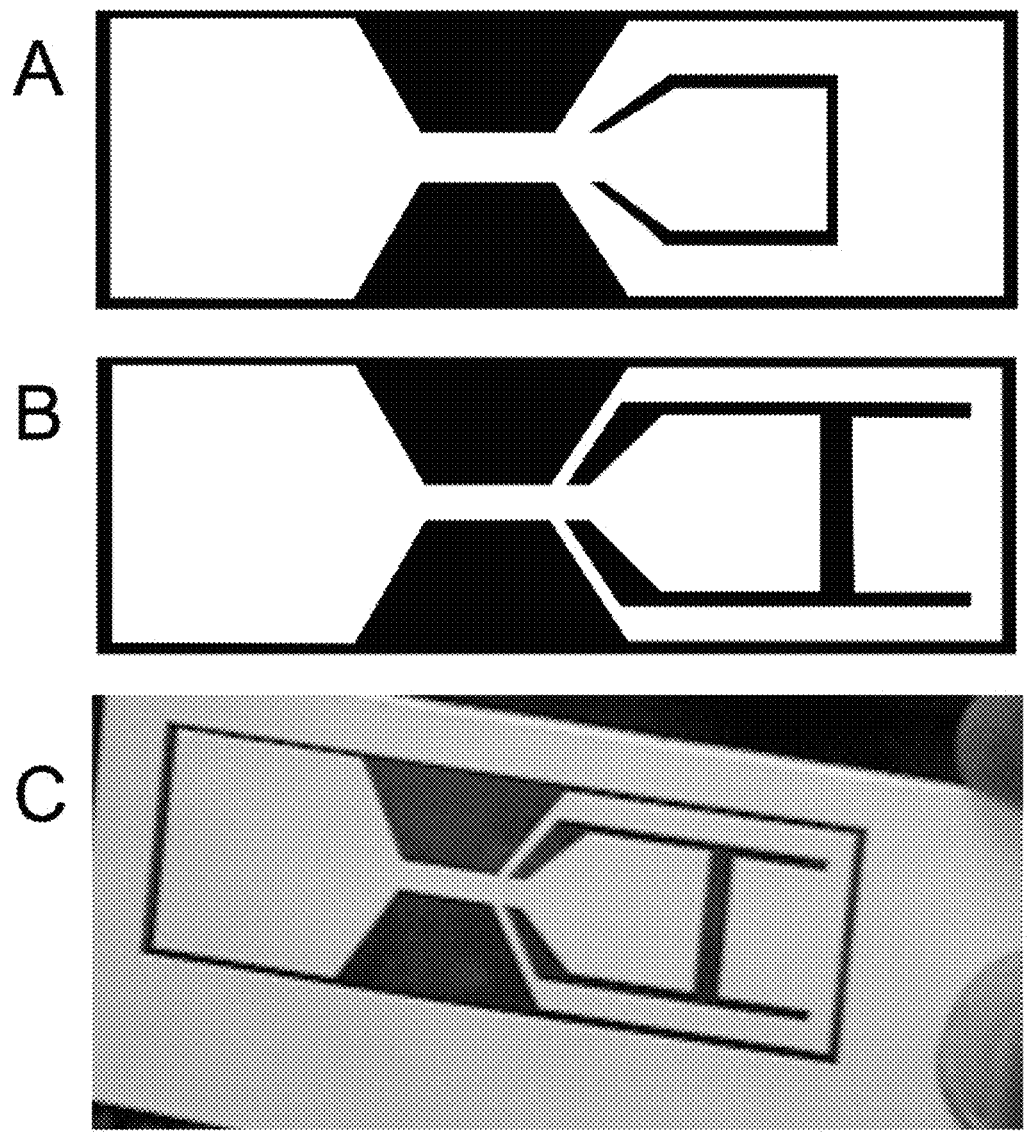
FIG. 7. Laser ablation of the nitrocellulose layer of backed nitrocellulose can be used to generate buffer exchange structures similar to those fabricated by cutting methods. (A) A pattern used for generating a two fluid input exchanger by means of ablation. (B) Another of example of a two solution exchanger pattern. (C) Backed nitrocellulose (HF-135, Millipore, Inc.) was laminated, using a double-side adhesive tape, to polycarbonate sheet and subject to laser ablation using the pattern shown in part (B).
Figure 14:
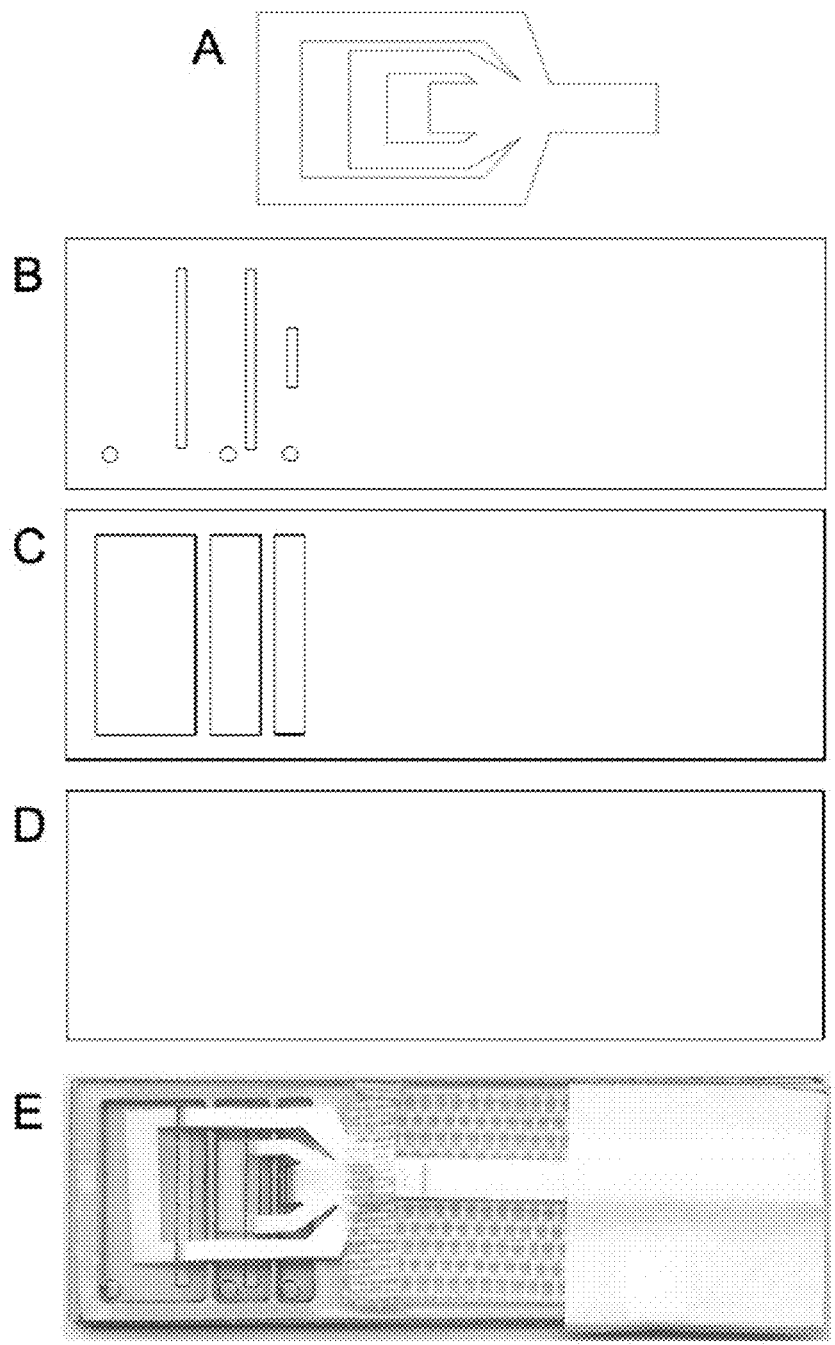
FIG. 14. Components of a self contained passive buffer exchange device. (A) An example three fluid exchanger suitable for integration with a simple supporting fluidic system. (B) Pattern for cutting polycarbonate to accommodate the fluid input tabs of the exchanger depicted in part (A). (C) fluid reservoir forming pattern for cutting polycarbonate sheet. Lamination to layer shown in part (B) carrying inserted exchange structure and to bottom layer shown in part (D) forms a integrated buffer exchange device allowing three solutions to be introduced via solution input ports. (D) Pattern for cutting bottom piece of device. (E) Scan of an assembled device shown here making use of 3 MM chromatography paper for the buffer exchange component interfaced to an immuno-assay strip. In the depicted device, immuno-assays are conducted by introducing sample to the right most port, staining reagent (antibody conjugated colloidal gold) to the middle port and a final wash buffer to reduce background is added to the left most port. All solutions are added at the time of assay initiation. The size of the device is 25 mm×75 mm, similar to a standard microscope slide.

To eliminate the need for electronic control systems, valves, and other fluid flow control schemes that require moving parts, applicants have developed various structures to mediate passive control of solutions through absorbent materials. These structures may be employed for the control of buffer and sample flow over, for example, a lateral flow substrate. Through the use of geometrically-defined flow paths in a lateral flow membrane, such as nitrocellulose, or in other absorbent materials such as chromatography paper, the flow rate of multiple solutions/buffers may be passively controlled. The lateral flow membrane may optionally comprise a single, integrated membrane. In one methodology, described further by way of the examples presented in Example 4, infra, nitrocellulose membranes are cut to form individual flow paths for different solutions, which flow paths vary by length and or width of the membrane (see, for example, FIGS. 4-9). In addition to the geometric shapes exemplified by the prototype devices shown in FIGS. 7, 8 and 14, one skilled in the art will readily appreciate that many other shapes can achieve the desired modulation of the multiple solution flow paths required by the assay it is intended to facilitate. In addition, although this aspect of the invention is exemplified by single nitrocellulose membranes in which all flow paths are seamlessly integrated, other systems will also be apparent, including but not limited to those in which flow paths are modulated not only by membrane flow path length and/or width, but also by interrupting sequences of materials other than the membrane material, such as cellulose esters, glass fiber, polyethersulfone, cotton, dehydrated polyacrylamide, silica gel, and polyethylene glycols.

Figure 4:
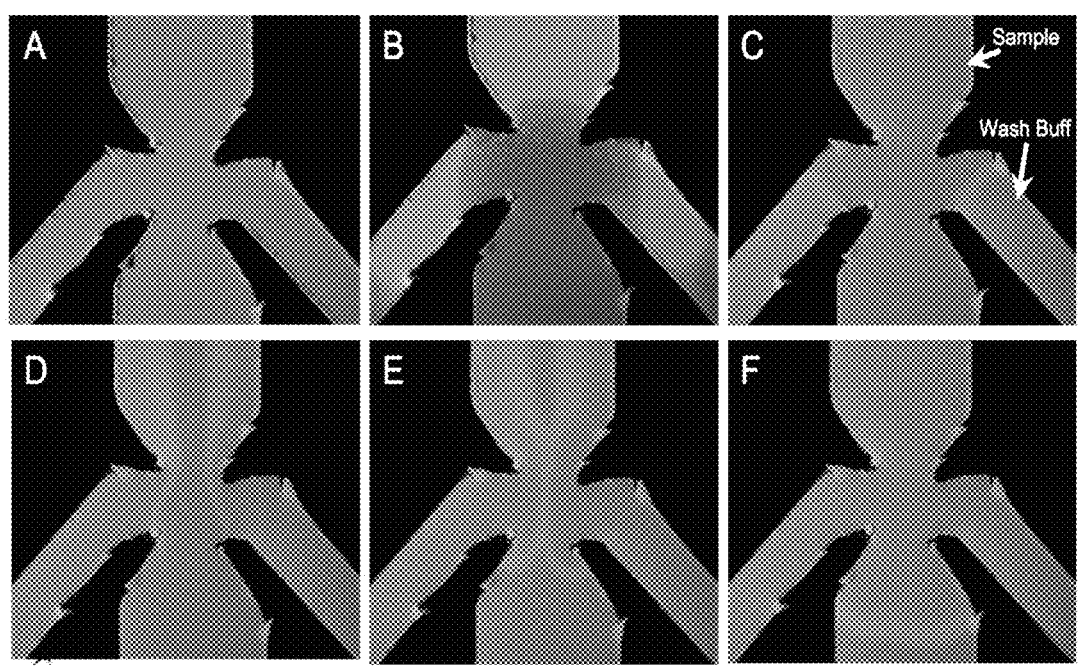
FIG. 4. Passive buffer flow control demonstrated on a prototype lateral flow device: (A) Passive buffer flow control geometry cut from nitrocellulose. (B) Sample (purple) and wash buffer (pink) have been introduced to wells of a 96 well titer plate and the passive buffer flow control device has been introduced to the wells such that the central flow path is emersed in sample and the flanking flow paths are placed in wash buffer. Sample solution is visible in the central flow path and flow path junction regions of the device. Wash buffer is visible near the edges of the panel. (C) Sample continues to flow over the capture zone (located at the top of the frame) as wash buffer migrates, by capillary flow through a path longer and more narrow than used for the sample path, to the main strip junction. (D) As sample is exhausted, wash buffer begins to displace sample buffer. (E) Sample has now completely traversed the capture zone and wash buffer begins to flood the capture zone. (F) Within 5 minutes wash buffer has completely replaced sample buffer.
Figure 5:
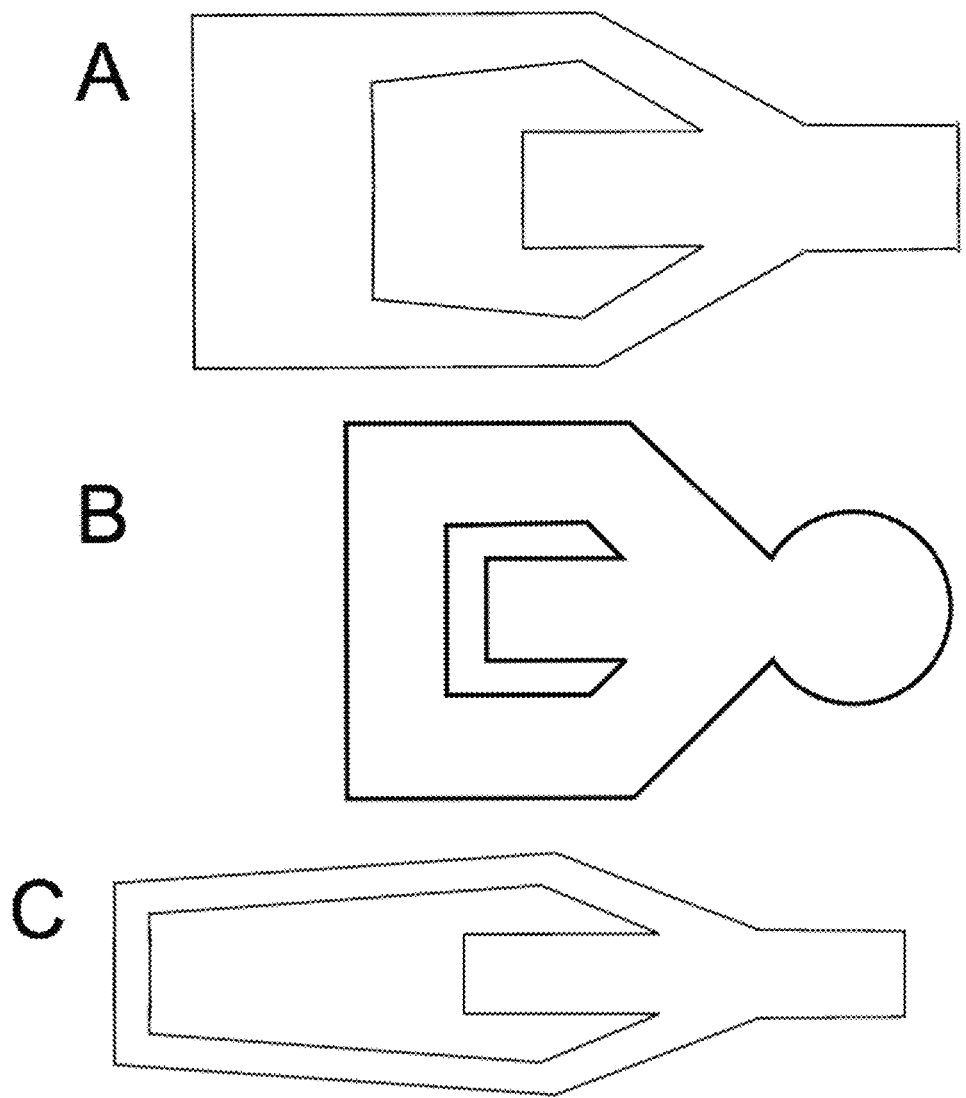
FIG. 5. Examples of buffer exchange structures which can be cut using a vinyl cutter or laser cutter from absorbent materials such as nitrocellulose or chromatography paper. The depicted structures support a system making use of two fluids. (A) Two fluid flow channels support a buffer exchange or reagent introduction. Sample may be introduced by employing a fluidic device such as described in Example 8. The central tab descends into a reservoir chamber to accommodate uptake of the primary solution. A second solution is introduced via the left most absorbent region of the structure. A larger volume of solution in the second reservoir assures that the second fluid replaces the first in the downstream regions of the substrate. (B) An example of a geometry used to accommodate circular punches of affinity matrices for nucleic acid or protein capture. (C) An example of a geometry with an extended second fluid path allowing the supporting fluidic system to accommodate larger fluid volumes.
Figure 6:
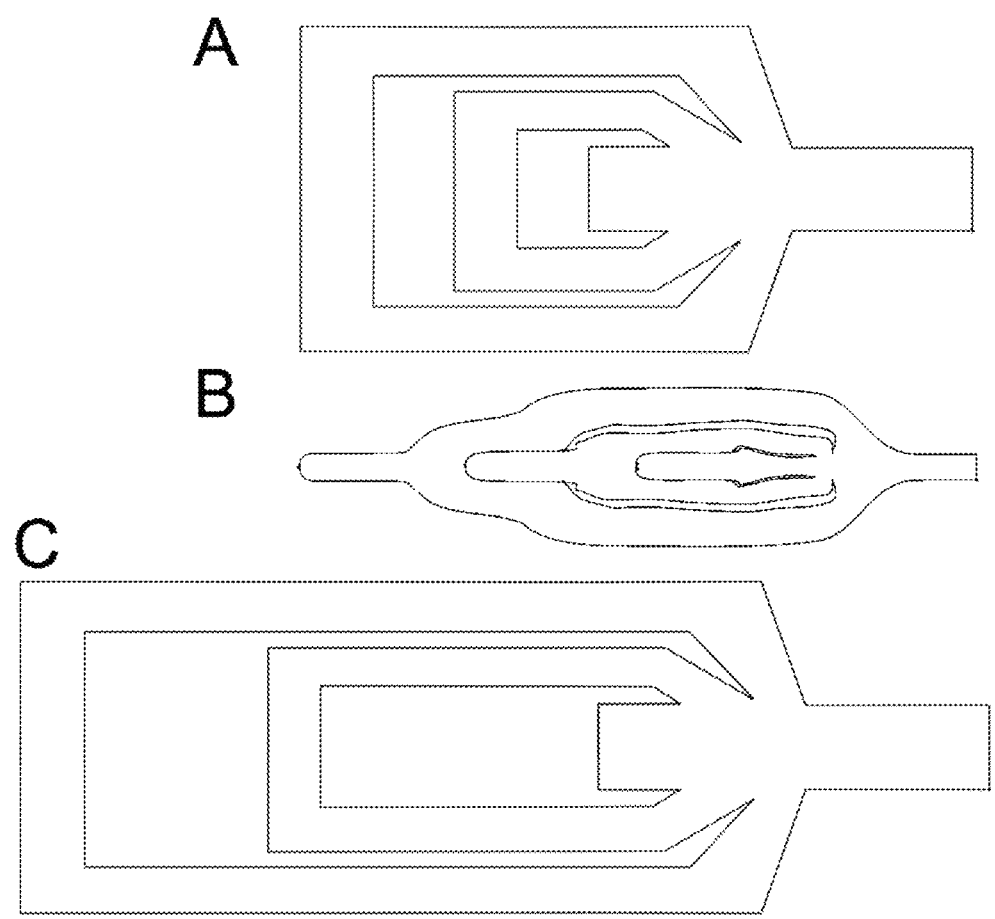
FIG. 6. Examples of buffer exchange structures which can be cut using a vinyl cutter or laser cutter from absorbent materials such as nitrocellulose or chromatography paper. The depicted structures support a system making use of three fluids. (A) A structure with three fluid input pads. The right most pad is used for sample application, the middle for a first buffer exchange e.g. a staining or wash buffer and the left most pad a final buffer exchange to accommodate, for example, a wash buffer or amplification reagent. This structure was been employed for immuno-assays making use of colloidal gold conjugated antibody as the first exchange buffer and a wash to reduce background as a second exchange buffer in a compact fluidic system (see also FIG. 14). (B) A structure with three fluid input tabs spaced to allow introduction to solutions in a 96 well plate. (C) A structure with three fluid inputs suitable for integration with simple polycarbonate fluidic system.
Figure 8:
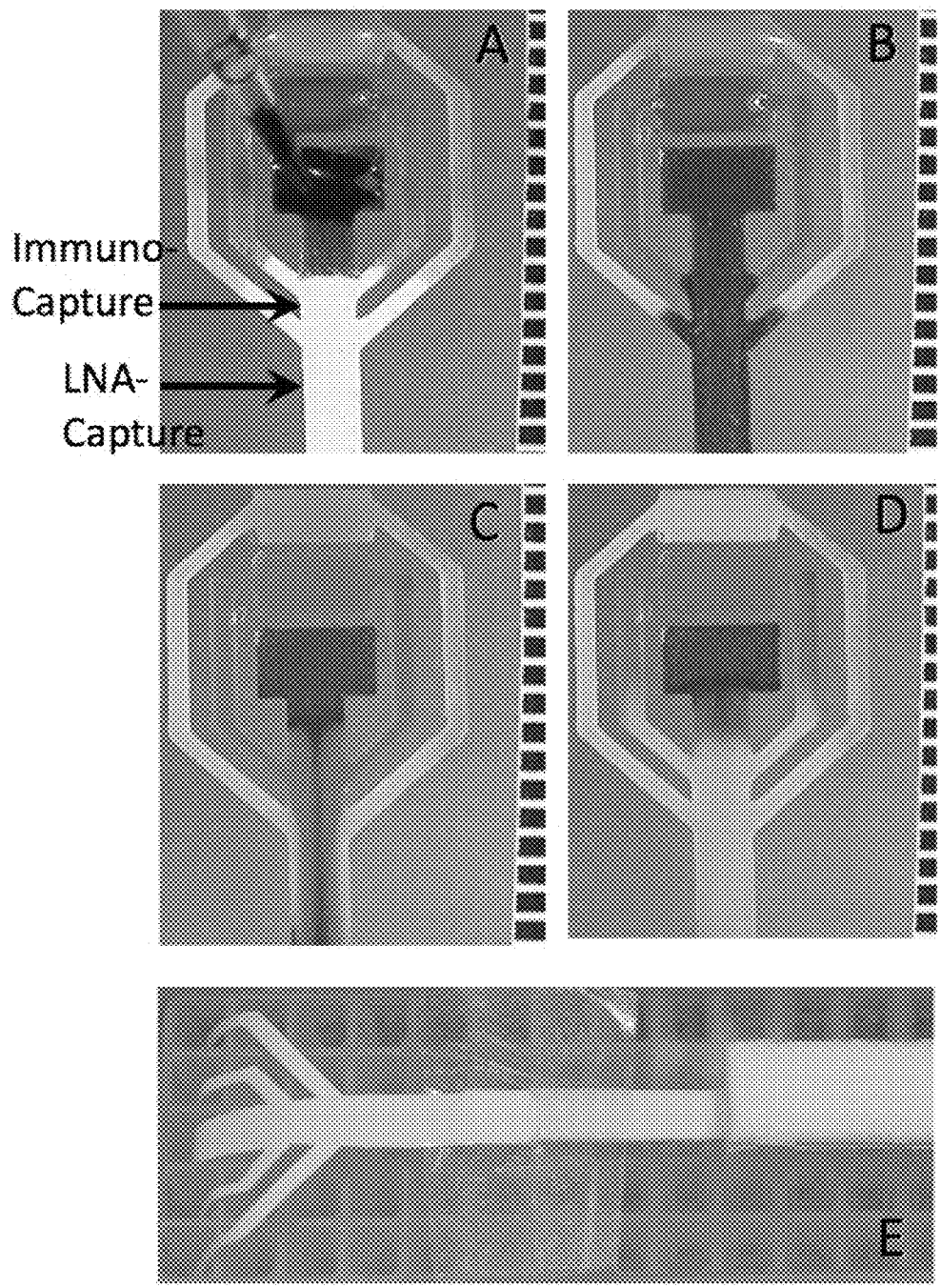
FIG. 8. Passive buffer flow control over a refined microfluidic nitrocellulose membrane substrate. (A) To demonstrate the utility of microfluidic nitrocellulose structures for accomplishing passive yet rapid and complete buffer exchanges, buffers carrying easily visualized dyes representing sample (blue), lysis buffer (red) and amplification buffer (yellow) were introduced to the device. (B) Sample flows over the immuno-capture zone through a wide membrane path, displacing lysis and amplification buffer to the membrane region proximal to the substrate walls until sample flow is exhausted. (C) As sample is exhausted, lysis buffer invades the immuno-capture zone disrupting captured particles and liberating nucleic acids for hybridization-based capture on LNA probes immobilized at the down-stream "LNA-Capture Zone" (indicated in part A). (D) Following exhaustion of the lysis buffer, buffer compatible with NASBA amplification washes the LNA-capture zone removing residual lysis buffer and facilitating hybridization of primers. Within 3 minutes three buffer exchanges are accomplished using 10 µL sample, lysis and amplification buffer volumes. The calculated bed volume of immuno- and LNA-capture zones is approximately 250 nL, thus each buffer exchange washes the capture zones with approximately 40 bed volumes. Further fluid flow modulation could be realized using additional flow paths of varying lengths and widths to allow further buffer washes and exchanges. Similarly, modulating the viscosity of the buffers could be used to further refine such assay parameters as incubation times in lysis buffer. Most significantly, device size can be altered to accommodate the processing of larger sample volumes. Ruler divisions at the right of each panel are 1 mm. (E) A breadboard three fluid buffer exchange system showing integration of buffer exchange nitrocellulose structure with an immuno-assay strip. This device was employed for immuno-capture and wash experiments described in Example 5.
Figure 9:
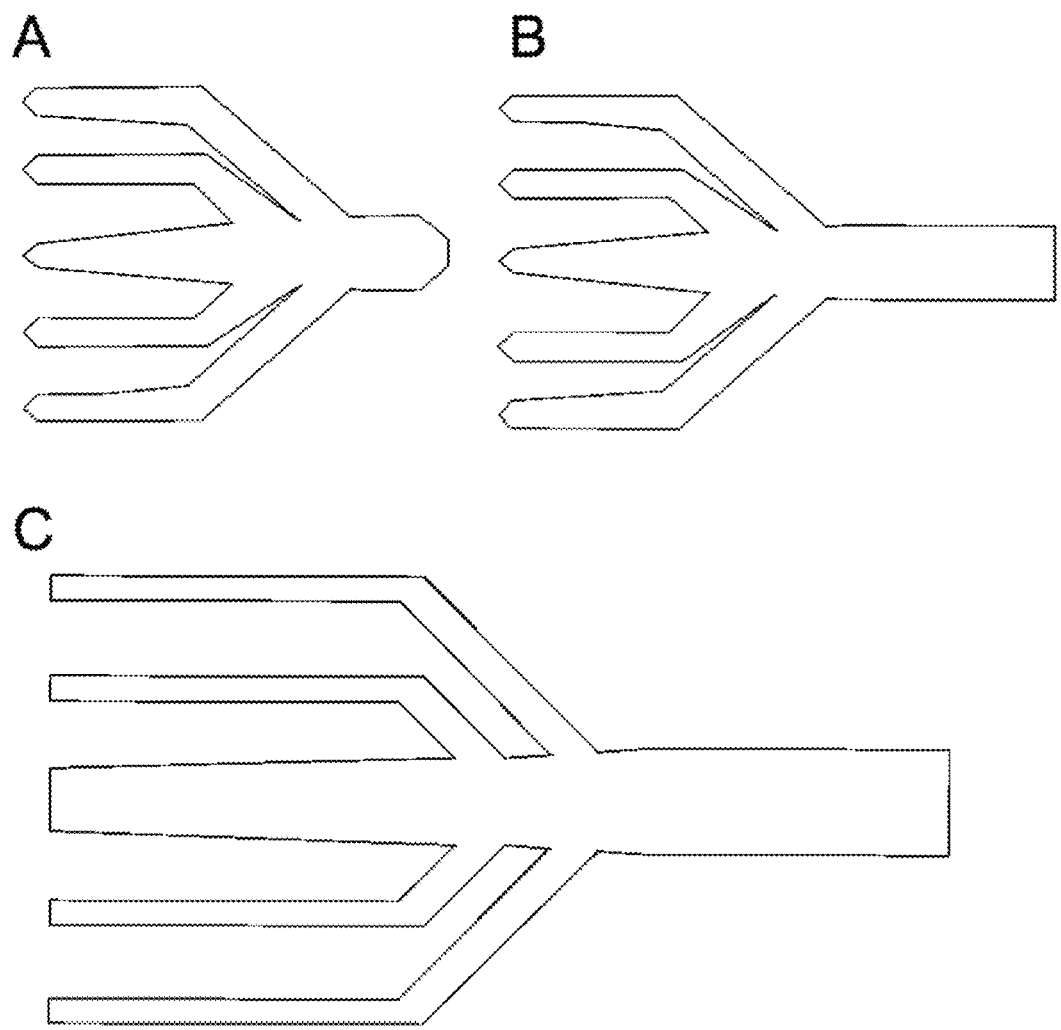
FIG. 9. Passive buffer exchange structures designed for use with 384 well titer plates. (A) A three fluid exchanger that makes use of five wells of a 384 well titer plate. The central fluid input occupies one well while second and third fluids are placed in well pairs flanking the central axis of symmetry. This structure was employed for nucleic acid capture from guanidinium isothiocyanate lysates as described in Example 7. (B) Another example of a 384 well compatible buffer exchange structure. (C) The buffer exchange structure used for experiments described in Example 6.

Additionally, by varying the viscosity of the solutions used the flow rate through the structure can be modulated to obtain differing behaviors. It will be appreciated that defining precisely controlled fluid paths and reaction sequences will vary according to the assay type and complexity. Significantly, during the course of concomitant flow of multiple solutions or buffers along the absorbent material the maintenance of laminar flow can be observed visually, as in FIGS. 4 and 8, when buffers of differing colors are employed. Further, FIGS. 4 and 8 illustrate that the solutions flowing through the more central regions of the structure exhibit a restriction of their flow path, giving rise to hydrodynamic focusing of the central solution resulting from the differing flow rates of the buffers traveling along more peripheral areas of the structure. This hydrodynamic focusing, characterized by, for example, the buffer flowing through the central region of the buffer exchange structure being constrained to a narrower central region of the structure's flow path, is a characteristic of the invention and can be readily observed in FIGS. 4 and 8. Based on the teachings provided herein, one will be able to empirically derive the necessary control for a specific assay with ordinary experimentation.

Figure 15:
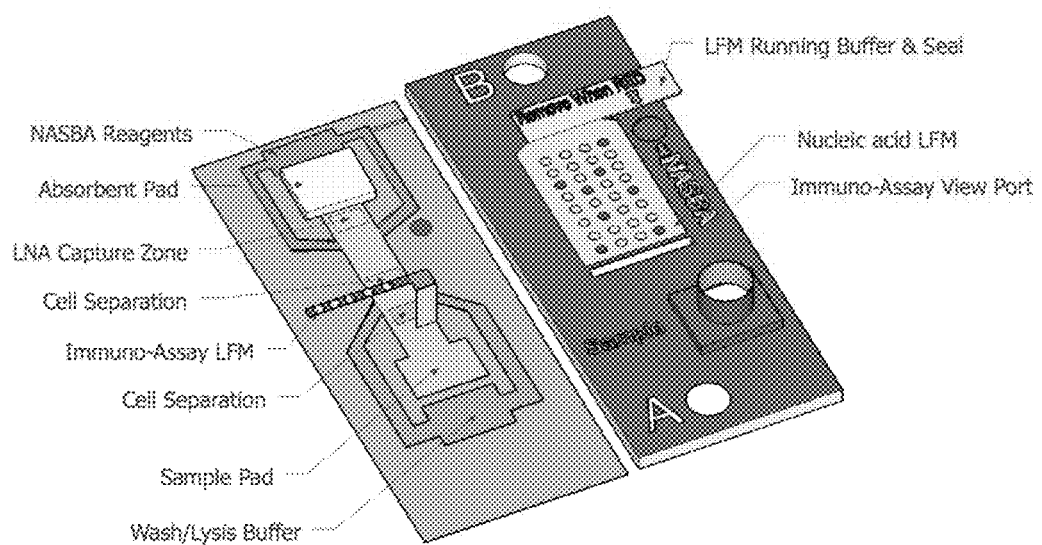
FIG. 15. Artists rendering of one possible embodiment of the proposed integrated sample preparation device. The different subsystems of the device's disposable component are depicted here as indicated. Fabricated from an inexpensive plastic housing and supported large pore nitrocellulose, the system will make use of capillary lateral flow and passive flow regulation to enable analyte affinity and hybridization-based capture as well as subsequent buffer exchanges required for lysis, washing and isothermal amplification by NASBA. 10% of the sample volume is interrogated immediately following sample addition using an immuno-assay LFM. Subsequent cell separation and lysis results in the liberation of cellular RNAs and stabilization by a guanidinium-based buffer. RNA sequences of interest are collected by hybridization in guanidinium buffer to LNA capture oligonucleotides. Any extracellular RNAs present in the sample should also be captured on the LNA oligonucleotides. Swab elution buffers may also be optimized for elution efficacy, immuno-assay compatibility and RNA stabilizing properties. For off-device analysis, a simple punch-out system could be incorporated to enable facile collection of cell separation or LNA capture zones (not shown).
Figure 16:
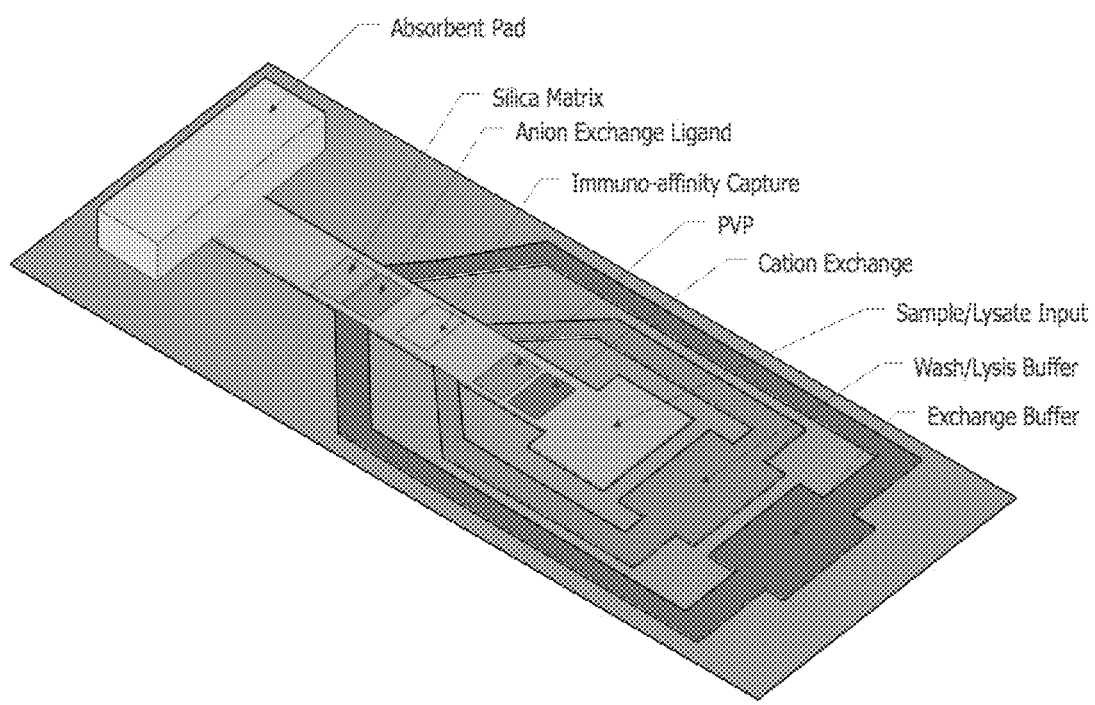
FIG. 16. Schematic of an alternative integrated device layout, which utilizes anion/cation exchange. A lateral flow strip accepts sample either in native buffer for immuno-affinity purification of cell and viral targets using an immobilized antibody ligand (Cell/Particle Capture) or as a lysate for affinity purification of nucleic acids by anion exchange (Anion Exchange Ligand). Depending on the input sample, a wash or lysis buffer is introduced at the time of protocol initiation to the Wash/Lysis zone where it flows from its absorbent pad (not shown) to the main substrate via a narrow nitrocellulose path reaching the main strip only after complete transport of the sample solution. Sample path treatments such as PVP, PVPP or cation exchange ligands may be included for amplification inhibitor removal. High ionic strength wash buffer elutes nucleic acids from the anion exchange ligand and provides an electrostatic environment supportive of efficient binding to the silica matrix. The resulting purified nucleic acids may be recovered by elution or collection of the silica matrix into a microcentrifuge tube carrying a frit where the nucleic acids may eluted using at least 2-bed volumes (>0.8 µL) of low ionic strength buffer (water, TE, etc).

Integrated Systems:

Also envisioned are fully integrated, sample-to-answer lateral flow assay devices that incorporate one or more elements of the present invention. Example integrated systems are schematically represented in FIGS. 15 and 16. For example, in one embodiment, a LFSP device is integrated with both immuno-assay screening and NASBA amplification followed by a downstream lateral flow sandwich hybridization nucleic acid assay. A schematic representation of such a device is shown in FIG. 15.

Such devices may comprise a lateral flow compatible chromatography support, such as HiFlow 135 large pore supported nitrocellulose (Millipore). This substrate is preferably patterned using a fluid deposition system such as a piezo-actuated picoliter deposition system (NanoPlotter 2.0, GeSim) to confer specific properties at desired locations in the sample flow. For example, regions up-stream of an immuno-capture zone are preferably treated to confer modifications capable of removing or reducing the activity of amplification inhibitors or other undesirable sample matrix contaminants. Antibodies to pathogens of interest are preferably located such that target particles are captured from sample solutions during capillary lateral flow. Further, by incorporating passive fluid flow control, captured cells or viruses can be lysed to liberate nucleic acids for affinity capture and purification at down-stream substrate zones. Some embodiments may be equipped with a heating element powered by a USB interface or internal or external power source or battery, to incubate sample in lysis buffer at an elevated temperature. Nucleic acids liberated during lysis then preferably flow to down-stream affinity capture zones for immobilization, washing and collection. The capture zone of the device may incorporate PCR, RT-PCR, NASBA or isothermal nucleic acid amplification reactions.

To allow the incorporation of more stringent washing conditions without significant increases in protocol complexity, the invention also supplies an approach that exploits the increased stability of LNA duplexes. In this scheme, the sample preparation device carries immobilized LNA oligonucleotides. These immobilized probes are predicted to allow sequence specific hybridization-mediated capture of target RNAs under the denaturing conditions imposed by a guanidinium-based lysis buffer. As known in the art, LNA oligonucleotide can be used to capture, by hybridization, RNA molecules present in crude cell lysates containing 4M guanidinium. LNA capture probes will be designed to hybridize to regions near but not overlapping with NASBA amplification primer binding sites.

One advantage of a supported nitrocellulose system is the ease with which chemical modifications can be made to the membrane. Prior reports have detailed methods for covalent and adsorptive modification of nitrocellulose to introduce immobilized functional groups for both cation and anion exchange chromatography. Treatments that result in an immobilized anion exchange ligand at a defined zone or component membrane of a multiple membrane system may also be included for nucleic acid binding and purification, including without limitation polyethyleneimine (PEI) as well as diethyl aminoethyl (DEAE) functional groups, both of which have been used for membrane based ion exchange chromatography. Additionally, regions up-stream of nucleic acid affinity ligand can be treated to reduce or preclude the transport of common nucleic acid sample contaminants. Such modifications could include, for example, polyvinylpyrrolidone (PVP), polyvinylpolypyrrolidone (PVPP), novel inhibitor sequestering agents and cation exchange ligands.

EXAMPLES

Example 1

NASBA Amplification of RNA from Crude Bacterial Cell Lysates

In order to evaluate the feasibility of using crude lysates to supply template RNA for amplification, the efficacy of NASBA amplification from *E. coli* lysates was examined. Lysates were prepared by adding varying quantities of *E. coli* liquid culture to cells-to-cDNA buffer (Ambion) and heating to 75° C. for 10 minutes. This method was reported to generate suitable template for RT-PCR (reverse transcriptase-polymerase chain reaction) from crude *L. moncytogenes* lysates [49]. Lysates were diluted 1:5 and 2 μL of the resulting material used in a 10 μL NASBA reaction.

A constitutively expressed mRNA, rpIV, was used as the NASBA target [50]. NASBA P1 and P2 primer sequences were as follows:

```
EC-rp1V-P1:
                                        [SEQ ID NO: 1]
5'-aattctaatacgactcactatagggagaaggCCATCGTTGTGTTC
AGCGTTA-3'
and EC-rp1V-P2:
                                        [SEQ ID NO: 2]
5'-gatgca aggtcg cat atg agAACTATCGCTAAACATCGCC
A-3'.
```

Lower case characters in the P1 sequence denote the T7 RNA polymerase promoter sequence. Lower case characters in the P2 sequence represent the tag sequence used for hybridization sandwich assay mediated detection. The sequences used for rpIV capture and detection on LFMs were the capture probe:

```
        rp1V-cap:
                                        [SEQ ID NO: 3]
        5'-CTGCTCAGAAGGTTCGCCTT-3'
``` and the detection probe:

```
UNI-det-5Tbio:
                                        [SEQ ID NO: 7]
5'-TT-U-biotin-TTTT-U-biotin-TTTT-U-biotin- TTTTTTT gat gca agg tcg cat atg ag-3'.
```

NASBA reactions were allowed to proceed for 60 minutes at 41° C. after which 4 μL was removed and assayed for rpIV amplicon by LFM using colorimetric detection mediated by dyed polystyrene microspheres conjugated to streptavidin.

The results presented in FIG. 1 show the LFM membranes following exposure to NASBA reactions containing crude lysate from the indicated number of cells. As few as 2000 cells could be detected by LFM, following NASBA amplification, using crude whole cell lysate to supply template. This experiment demonstrates that a crude lysate prepared under denaturing conditions in the presence of guanidinium can be used successfully as NASBA template. Given that one proposed lateral flow method for sample preparation would allow a sequence-specific capture of the target RNA and stringent washes in guanidinium buffer, it is likely that the detection limit of 2000 cells obtained with crude lysate can be significantly improved.

Example 2

Lateral Flow Concentration of Analyte and Subsequent Amplification from TMV Particles Contained within Leaf Tissue In this Example, the utility of lateral flow facilitated immune-capture as a means of concentrating analyte prior to nucleic acid isolation or amplification was investigated with tobacco mosaic virus (TMV).

Figure 2:
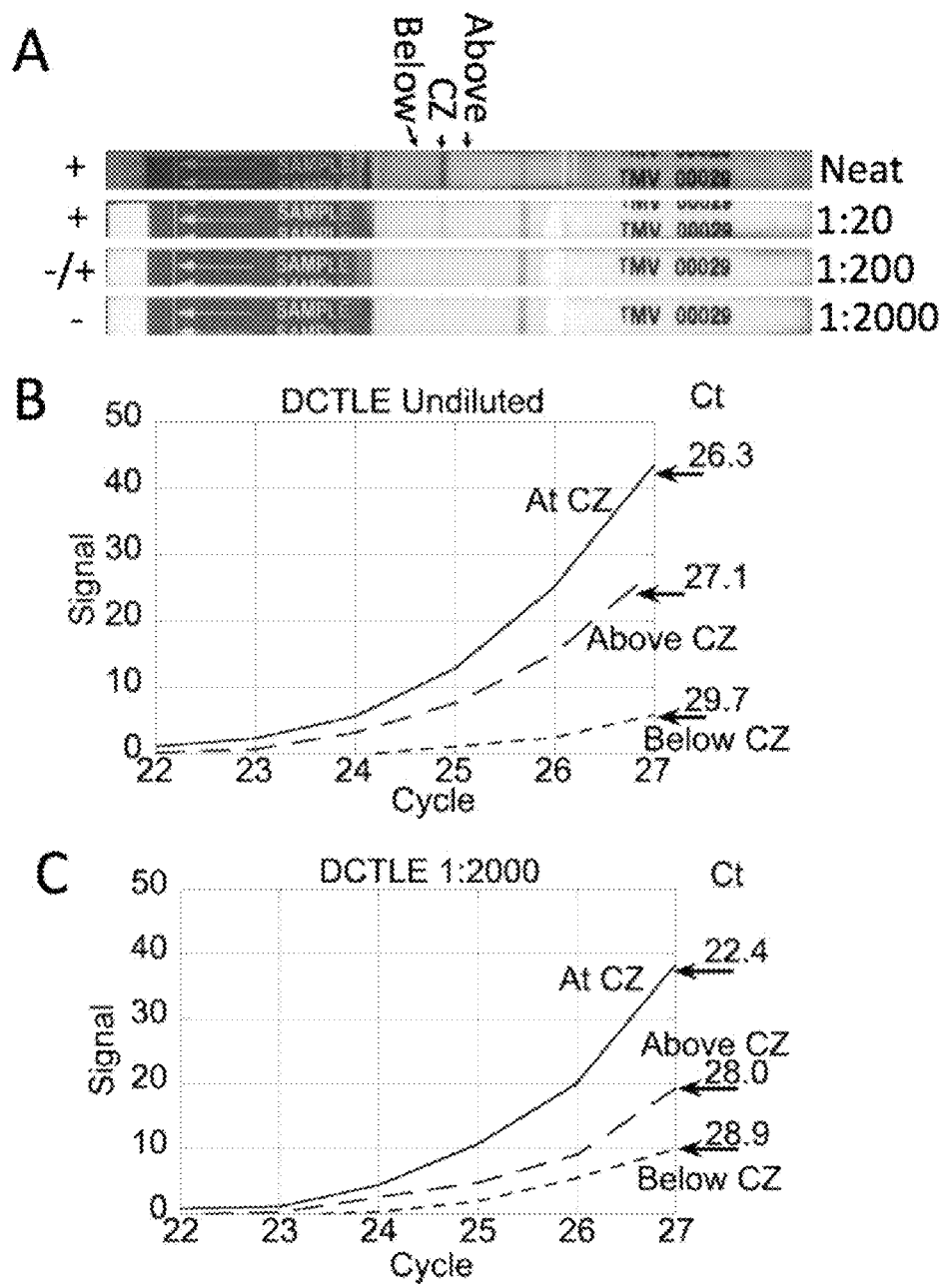
FIG. 2. Lateral flow lateral flow facilitated immuno-capture. (A) Agdia TMV immuno-assay strips were run using 200 µL of the indicated dilution of dried cure tobacco leaf extract (DCTLE) in SEB1 extract buffer (Agdia, Inc.). DCTLE was generated by crushing 100 mg of dried cured tobacco leaf in 3 ml SEB1 extract buffer (Agdia, Inc.) in a plastic bag containing an abrasive mesh (Agdia, Inc.). Dilutions of 1:200 and greater were negative by immuno-assay. (B) Real-time reverse-transcriptase PCR(RT-PCR) was used to examine regions below, at and above the TMV capture zone (CZ). 200 µL of undiluted extract was subjected to lateral flow and subsequent real-time RT-PCR of strip regions below, at and above the capture zone. A strip region from below the CZ revealed little or no detectable amplification with a cycle threshold (Ct) value of 29.7. A sample taken from the CZ generated a strongly positive signal for TMV with a Ct value of 26.3. A region above the capture zone also resulted in positive detection with a Ct value of 27.1. Thus, neat extract generated clearly positive PCR reactions only at and above the CZ while the region below the CZ inhibited PCR amplification. These data demonstrate that simple lateral flow immuno-capture without washes or further manipulation can alleviate PCR inhibition both through concentration of target particles and through physical sequestration of inhibitory matrix constituents. Significantly, the region above the CZ in the neat extract generates a positive PCR reaction apparently as a result of viral particle bleed-through from the CZ and an apparent concomitant depletion of inhibitors. (C) Real-time reverse-transcriptase PCR(RT-PCR) was used to examine regions below, at and above the TMV capture zone (CZ) of TMV immuno-assay test strips following challenge with 200 µL of a 1:2000 dilution of DCTLE in sample buffer. A strip region from below the CZ revealed only weak amplification suggesting at this dilution inhibitors became sufficiently dilute to allow some amplification to take place (Ct=28.9). A sample taken from the CZ generated a strongly positive signal for TMV with a Ct value of 22.4 suggesting that the combined effect of inhibitor dilution and immuno-capture mediated virus concentration conspire to enable more robust amplification relative to neat extract experiments (compare with part A). A region above the capture zone also resulted in positive detection with a Ct value of 28.0.
Figure 3:
FIG. 3. EtBr stained gel of RT-PCR products showing gel electrophoretic analysis of RT-PCR reactions conducted on samples processed with PVP treated and untreated sample pads in conjunction with standard lateral flow strips. PVP sample pads alleviate PCR inhibition resulting from exogenously added humic acid. DCTLE was generated as for FIG. 2. 200 µL aliquots of extract were spiked with 0, 12, 25 ng of humic acid and subjected to lateral flow immuno-capture of TMV using either a standard sample pad (Untreated Pad) or a sample pad treated with 10% polyvinylpyrrolidone (molecular weight 360,000) (PVP Samp Pad). Capture zones were collected and subjected to RT-PCR. Although 12 ng and 25 ng humic acid supplemented extracts failed to generate detectable PCR products following TMV capture using lateral flow strips with untreated sample pads, all samples exhibited detectable PCR products when subjected to immuno-capture using PVP treated sample pads. Interestingly, 0, 12 and 25 ng humic acid samples run on PVP treated sample pads exhibited improved PCR amplification relative to 0 ng controls processed with the untreated pads. Lane labeled "RNA" is a positive control making use of total tobacco RNA preparations made using RNeasy (Qiagen).

FIG. 2A-C depicts the results of immuno-affinity capture and concentration of tobacco mosaic virus (TMV) particles during lateral flow of 200 µL of crude macerated tobacco and subsequent amplification (reverse-transcriptase-PCR) reactions programmed with regions of the lateral flow substrate below (proximal to the sample pad), at and above (distal to the sample pad) the immune-capture zone (as shown in FIG. 2A). The capture zone is greatly enriched in virus particles while the relative concentration of inhibitory constituents is reduced. The 1000-fold reduction of sample volume from 200 μL to 200 nL, based on the calculated bed volume of the capture zone, exhibited here will also facilitate subsequent washing to further reduce inhibitor concentrations.

These data demonstrate that lateral flow can be used to not only concentrate dilute analytes to a spatially defined capture zone but that regions of the device downstream of the capture zone are depleted with respect to the captured species. These data support applicant's hypothesis that simple lateral flow immuno-assay methods can form the basis for a rapid and cost effective immuno-affinity purification system for separation and preparation of complex biological samples, as well as the assertion that appropriately treated substrates can be used to deplete samples of unwanted constituents at downstream capture zones.

Example 3

Lateral Flow Reduction of Amplification Inhibitors Using Polyvinylpyrrolidone This Example shows that polyvinylpyrrolidone treated sample pads can deplete PCR inhibitors via lateral flow.

Crude sample constituents inhibitory to PCR can be depleted during lateral flow; thus specific substrate treatments may further facilitate amplification of nucleic acids from captured target cells or particles. To test this hypothesis, absorbent sample pads were treated with a 10% solution of polyvinylpyrrolidone (MW=360,000) and RT-PCR amplification of TMV concentrated from macerated leaf tissue following lateral flow immuno-capture (Example 2, supra) on devices carrying either PVP treated or untreated sample pads was evaluated.

These reactions made use of previously reported primer sets for TMV detection. Neat tobacco extract added directly to RT-PCR reactions was negative for TMV without prior immuno-capture to deplete inhibitors. Consistent with this interpretation, 1:50 dilutions of extract were positive by PCR presumably due to lower inhibitor concentrations.

As shown in FIG. 3, PVP sample pads alleviated inhibition from exogenously added humic acid, a potent PCR inhibitor, while untreated sample pads did not. Perhaps most significantly, the use of PVP treated sample pads resulted in significantly improved amplification relative to untreated sample pads even in the absence of exogenously added inhibitor. Although 12 ng and 25 ng humic acid supplemented extracts failed to generate detectable PCR products following TMV capture using lateral flow strips with untreated sample pads, all samples exhibited detectable PCR products when subjected to immuno-capture using PVP treated sample pads (FIG. 3). Interestingly, 0, 12 and 25 ng humic acid samples run on PVP treated sample pads exhibited improved PCR amplification relative to 0 ng controls processed with the untreated pads (FIG. 3).

Example 4

Geometric Architectures for Passively Controlling Multiple Solution Flows in Lateral Flow Systems This Example shows prototypes of passive lateral flow buffer control systems utilizing attributes of geometrically-defined nitrocellulose strips to control the speed and volume of fluid flow. In order to rapidly generate prototypes of nitrocellulose or other adsorbent material-based devices, methods were developed for cutting miniaturized structures from sheets of absorbent material using either a vinyl cutter (Roland GX-24 CAMM-1) or a laser cutting/engraving system (VersaLaser VL-300 equipped with a 30 W CO2 laser (Universal Laser Systems, Inc.)) (FIGS. 4-9). Additionally, it was found that laser ablation of nitrocellulose from backed nitrocellulose sheets allows the fabrication of planar nitrocellulose structures suitable for use as fluid flow control and buffer exchange components (FIG. 7). A number of different shaped nitrocellulose structures were evaluated for their utility in exchanging two (FIG. 4, FIG. 5 and FIG. 7) and three fluids (FIGS. 6, 8 and 9) by means of passive capillary wicking in lateral flow mode.

Fluid flow control was performed using the prototype device shown in FIG. 4. In this crude prototype, two different buffer solutions migrate at different rates by capillary flow through variable paths defined by differing geometric attributes cut into the nitrocellulose strips.

A more refined prototype device was fabricated using the vinyl cutter, and is shown in FIG. 8A-D. By varying the length and widths of the nitrocellulose paths defined for different solutions, this device was able to manage the temporal control of three different solutions relative to defined reaction zones on the device. As shown in FIG. 8, sample, lysis buffer, and amplification buffer are introduced to the device (FIG. 8A). Sample buffer flows over the immuno-capture zone through a wide membrane path, displacing the lysis and amplification buffers to the membrane region proximal to the substrate walls until sample flow is exhausted (FIG. 8B). As sample is exhausted, lysis buffer invades the immuno-capture zone disrupting captured particles and liberating nucleic acids for hybridization-based capture on LNA probes immobilized at the down-stream "LNA-Capture Zone" (indicated in FIG. 8A). Following exhaustion of the lysis buffer, buffer compatible with NASBA amplification washes the LNA-capture zone removing residual lysis buffer and facilitating hybridization of primers. Within 3 minutes, three buffer exchanges are accomplished using 10 μL sample, lysis and amplification buffer volumes. The calculated bed volume of immuno- and LNA-capture zones is approximately 250 mL, thus each buffer exchange washes the capture zones with approximately 40 bed volumes. Further fluid flow modulation could be realized using additional flow paths of varying lengths and widths to allow further buffer washes and exchanges. Similarly, modulating the viscosity of the buffers could be used to further refine such assay parameters as incubation times in lysis buffer. Most significantly, device size can be altered to accommodate the processing of larger sample volumes. Ruler divisions at the right of each panel are 1 mm.

Example 5

Geometric Architectures for Passively Washing Immunocaptured Targets to Increase Amplification Efficiency Results obtained from experiments employing real-time detection of RT-PCR amplicons as well as LFM detection of NASBA reaction products indicated that residual inhibitory constituents of the sample matrix remain associated with immuno-captured virus or remain in the included bed volume of the chromatography substrate. These data suggested that a buffer wash following lateral flow immuno-capture may provide a simple but effective means of increasing amplification efficacy from complex sample matrices. To test this hypothesis, lateral flow strips were subjected to a buffer wash prior to capture zone harvest and nucleic acid amplification by laminating a nitrocellulose structure designed to mediate passive buffer exchange onto a nitrocellulose immunoassay strip carrying an anti-TMV antibody at the capture zone line and a control antibody capable of binding colloidal gold conjugated detection antibody at a control line.

To minimize the level of user intervention required to accomplish buffer washes of lateral flow substrates, lateral flow strips were laminated to backed nitrocellulose cut into shapes designed to accomplish passive buffer exchange. These devices allowed rapid exchange of sample with wash buffer and a final equilibration in ultrapure H2O prior to PCR to reduce the potential impact of residual wash buffer on PCR performance. The device used is shown in FIG. 8E. A 100 μL sample volume was used. Wash buffer volume was 50 μL followed by a final rinse using 25 μL of $H_2O$ to remove residual buffer constituents. Sample, wash buffer and H2O were added to the corresponding wells of a 384 well plate at the time of assay initiation. Following completion of capillary transport, capture zones were harvested and subjected to analysis by real-time RT-PCR.

To identify buffers with a composition compatible with immuno-affinity immobilization of virus at the capture zone of lateral flow strips, the effect of various wash buffers on TMV immuno-strip capture zone signals generated using neat tobacco extract were evaluated. These studies revealed no visually detectable elution of sequestered gold particles from the capture zone following capillary wicking of 200 μL of an ethanol containing wash buffer, referred to here as NME (0.5M NaCl, 50 mM MOPS pH 7.0, 15% ethanol). In contrast to the effect of NME on capture zone signals, the guanidinium isothiocyanate containing buffer RLT (Qiagen, Valencia, Calif.) rapidly cleared the capture zone of detection particles.

Figure 10:
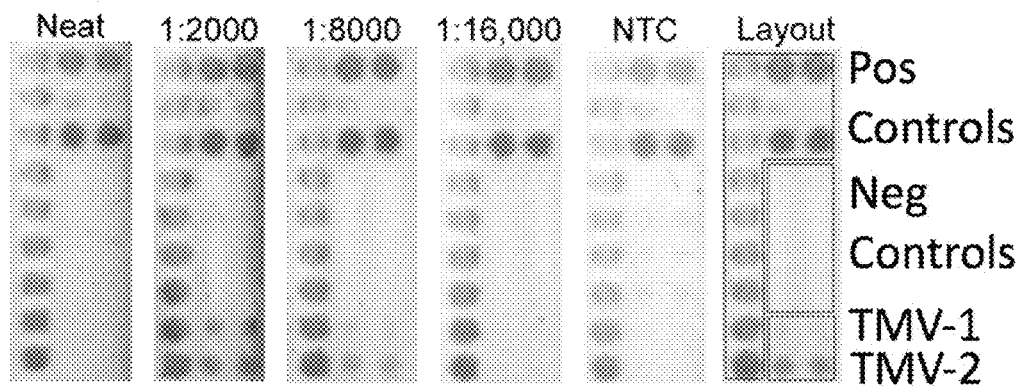
FIG. 10. LFM detection of TMV following dilution of tobacco extract in SEB1 sample buffer. DCTL strips modified to carry a buffer exchange nitrocellulose structure designed to accommodate sample, wash buffer, and a final H2O rinse in a 384 well plate format (see FIG. 8E and FIG. 9C). Soil extracts were generated using 3 g of soil in 30 mL of SEB1 extract buffer. Sample volume was 100 µL. Washes were conducted using 50 µL of NME buffer and were followed by a 25 µL H2O equilibration. Soil RNA isolated using a Qiagen RNeasy kit was included as a negative control. Without the wash step, but with the 25 µL H2O rinse, 1:2000 and 1:4000 dilutions generated high Ct values of 28.2 and 28.3 respectively. Inclusion of a 75 µL NME buffer wash generated positive detection of TMV with 1:2000 sample exhibiting a Ct value of 26.2 and 1:4000 samples a Ct of 27.2.
Figure 10:
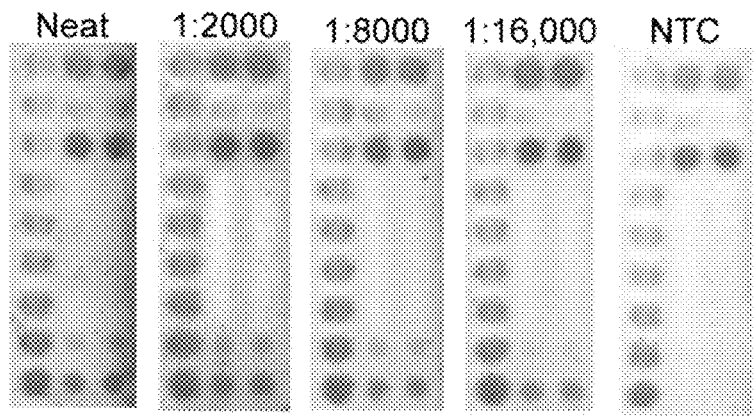

Using a 50 μL NME wash following challenge of TMV immuno-assay strips laminated to the passive buffer exchange structure with varying dilutions of DCTLE in SEB1, capture zones were harvested and subjected to NASBA amplification and amplicon detection by LFM. These studies revealed an alleviation of NASBA amplification inhibition previously observed in reactions programmed with capture zone material harvested from strips exposed to undiluted DCTLE (compare FIG. 10A with FIG. 10B). Additionally, the NME buffer wash resulted in detection of TMV at DCTLE dilutions of at least 1:16,000 suggesting that the more thorough removal of the SEB1 extract buffer employed for DCTLE dilutions from the chromatography substrate further increased amplification efficiency.

LFM detection of TMV amplicons made use of capture probes TMV-1 and TMV-2 immobilized on the LFM substrate:

TMV-1:
[SEQ ID NO: 5]
5' TTATGCTATAACCACCCAGG 3'

TMV-2:
[SEQ ID NO: 6]
5' TTATGCTATAACCACCCAGGACGCGATGAAAAACGTCTGGCAA 3' and a detection probe:

UNI-det-5Tbio:
[SEQ ID NO: 7]
5'-TT-U-biotin-TTTT-U-biotin-TTTT-U-biotin-

TTTTTTT gat gca agg tcg cat atg ag-3' visualized by streptavidin conjugated dyed polystyrene microsphere (Spherotech) capture.

NASBA amplification of TMV diagnostic sequence was accomplished using:

TMV-P1:
[SEQ ID NO: 8]
5' aat tct aat acg act cac tat agg g aga GAA AGC GGA CAG AAA CCC GCT Ga 3'

TMV-P2:
[SEQ ID NO: 9]
5' gat gca agg tcg cat atg ag GAC CTG ACA AAA ATG GAG AAG ATC T 3'

The TMV-P2 primer incorporates a tag sequence into the NASBA product that is capable of hybridizing to the UNI-det-5Tbio oligonucleotide to mediate detection.

Example 6

Use of Passive Buffer Exchange to Detect Trace Virus in a Complex and Inhibitory Sample Matrix Studies making use of tobacco extract revealed that the high viral titer in these samples allows PCR-based detection of TMV to be accomplished by simply diluting extract to a sufficient extent that inhibitors in the crude lysate fall below a critical concentration. To better evaluate the utility of a lateral flow immuno-capture step to render inhibitor laden samples containing low titers of target virus amenable to amplification, samples making use of soil extracts were devised to contain sufficient enzymatic inhibitor concentrations to completely abrogate PCR amplification of TMV diagnostic sequences in the absence of an intervening sample processing procedure. These samples allow an assessment of the impact of lateral flow immuno-capture on PCR-based detection schemes and provide an approach to evaluate the impact of a buffer wash on the level of amplification inhibition. To provide a challenging inhibitor laden sample, DCTLE was diluted 1:2000 or 1:4000, as indicted in FIG. 11, into a PCR inhibitory soil extract prepared using 3 g locally gathered soil measured into 50 mL polypropylene centrifuge tubes and vortexed vigorously in 30 mL SEB1 extraction buffer (Agdia, Inc.) and allowed to rotate overnight at room temperature. The resulting soil slurry was allowed to settle for 3 minutes prior to the collection of aliquots for RNA isolation, PCR testing for TMV or preparation of soil extracts spiked with DCTLE.

Figure 11:
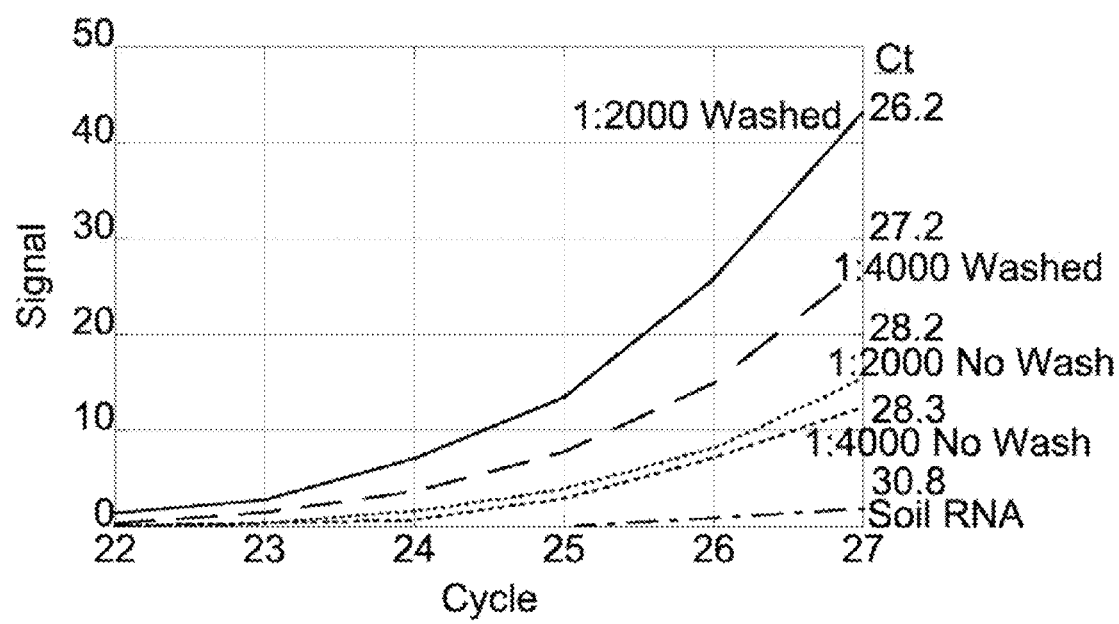
Figure 12:
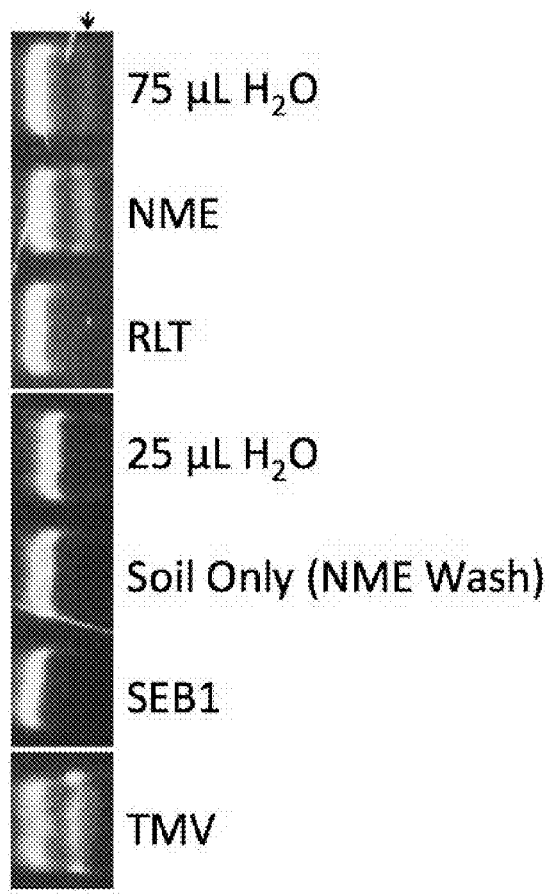
FIG. 12. Gel electrophoretic analysis of PCR reactions conducted on samples subjected to various wash treatments using passive buffer exchange washes of TMV immuno-captured from a highly inhibitory soil extract. Soil extract was spiked with DCTLE to give a final dilution of 1:2000 with respect to DCTLE. The volume of sample was 100 µL while NME washes were 50 µL and the final H2O rinse was 25 uL. The final H2O equilibration reduced the potential for carry-over of residual wash buffer into subsequent PCR reactions. Washes using 50 µL of water followed by a 25 µL water rinse (labeled as 75 µL H2O) generated a faint PCR product. The use of NME wash buffer generated robust PCR amplification (NME). Washes with RLT, a Qiagen guanidinium-based lysis buffer, failed to generate detectable PCR amplicon (RLT). Eliminating the 50 µL wash but retaining the 25 µL rinse failed to sufficiently reduce inhibitor concentrations as evidenced by the lack of detectable amplicon in these samples (25 µL H2O). Soil extract sample without added TMV subjected to NME wash did not generate detectable TMV amplicon (Soil Only (NME wash)). SEB1 extraction buffer alone was assayed as a further negative control (SEB1). Additionally, negative control immuno-capture experiments were conducted using virgin soil extract and a NME buffer wash to further establish the absence of TMV from the soil used. The TMV lane is a positive control PCR reaction programmed with RNA isolated from tobacco using the Qiagen RNeasy kit.

Capture zones were collected following completion of sample and wash buffer transport and introduced to reverse-transcriptase reactions followed by real-time PCR using 1 μL of the RT reaction as template. To characterize soil extracts, soil extract total RNA was isolated using Qiagen RNeasy protocols and assayed for TMV by real-time RT-PCR to confirm the matrix was negative for TMV. Additionally, DCTLE spiked soil derived sample matrix generated false negative real-time RT-PCR results using capture zones harvested from TMV assay strips challenged with 100 μL of soil extract containing either 1:2000 or 1:4000 DCTLE (FIG. 11). Passive capillary flow mediated wash of TMV assay strips challenged with soil extract containing tobacco extract at a final dilution of 1:2000 using 50 μL of NME buffer generated a positive real-time RT-PCR result (Ct 26.2) (FIG. 11) as well as a clearly identifiable band in agarose gels (FIG. 12, NME). Washes with 50 μL of RLT buffer did not result in successful TMV detection by either RT-PCR and gel analysis (FIG. 12, RLT) or by real-time RT-PCR (not shown). Additionally, a more dilute solution of DCTLE in soil extract, 1:4000, also generated positive TMV detection by real-time RT-PCR (FIG. 11) with a Ct value of 27.2 when a 50 μL NME buffer wash was employed prior to capture zone harvest.

Example 7

Geometric Architectures for Passively Washing Nucleic Acids Bound to an Affinity Matrix To evaluate the capacity of the passive buffer exchange approach to allow nucleic acids to be directly captured from a guanidinium lysate, tobacco lysate was prepared by maceration of dried cured tobacco leaf in Qiagen RLT guanidinium isothiocyanate lysis buffer using 22 μg of tobacco per μL RLT. A device for lateral flow chromatography and buffer exchange was fabricated using a laser cutter (VersaLaser VL-300, 30 W CO2 laser, Universal Laser Systems). The device was designed such that the input tails of the buffer exchange component were spaced at 4.5 mm intervals to allow sample and buffer to be absorbed from the wells of a 384 well plate. The distal end of the buffer exchanger was laminated to a 3 mm diameter punch taken from a Qiagen RNeasy column. This silica RNA binding matrix was used to evaluate the suitability of capillary lateral flow mediated buffer exchange to support viral RNA capture. Other materials, such as glass fiber filter material, may also be employed. Similarly, using other buffer systems, DEAE membranes could be incorporated into a similar system.

Figure 13:
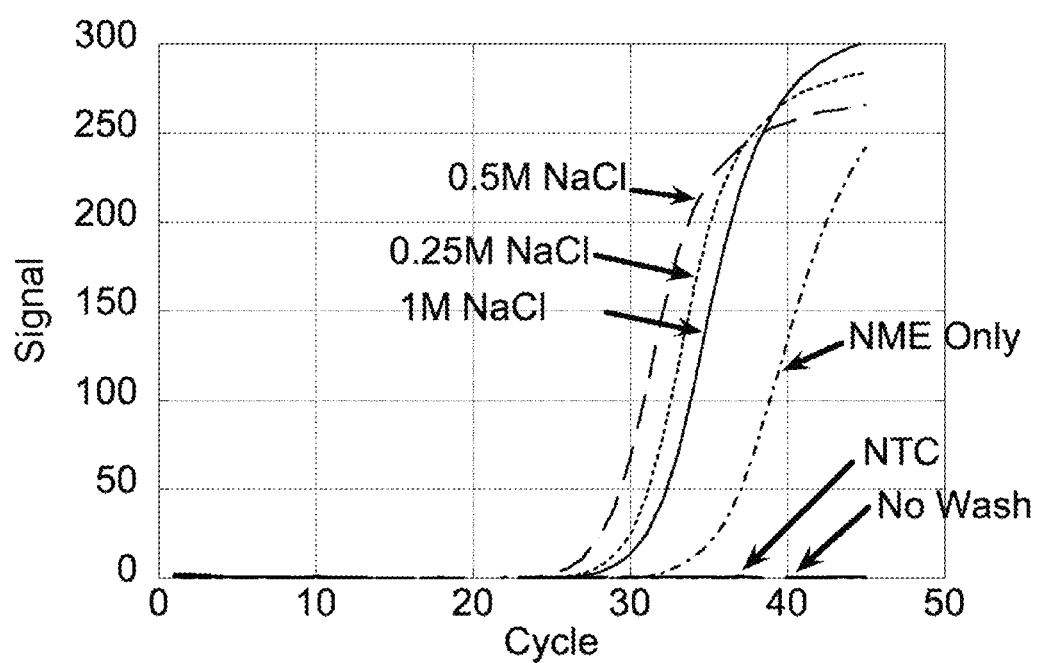
FIG. 13. Real-time RT-PCR analysis of an RNA binding matrix challenged with dried cured tobacco leaf lysate generated by crushing 22 µg/µL of tobacco in RLT guanidinium isothiocyanate-based lysis buffer (Qiagen, Inc.). Tobacco leaf lysate was subjected to lateral flow mediated nucleic acid capture using a nitrocellulose buffer exchange device of the structure shown in FIG. 9A laminated to a 3 mm biopsy punch of an RNeasy column silica RNA binding matrix, 10 µL of RLT tobacco extract was used as the sample. 40 µL washes were conducted using NME buffer for all treatments except the no wash control. The initial NME wash was followed by 80 µL of NME (NME Only), or NaCl at concentrations varying from 0-1 M as indicated. This aspect of the invention is described further in Example 7.

10 μL of RLT tobacco extract was used as the sample. 40 μL washes were conducted using NME buffer for all treatments except the no wash control followed by 80 μL of NME, or NaCl at concentrations varying from 0-1 M as indicated in FIG. 13. These data show that the NME wash followed by a 0.5M NaCl wash provided the best amplification of the conditions tested. Samples that were not washed failed to generate detectable real-time RT-PCR products.

Example 8

Integration of Passive Buffer Exchange Geometric Architectures into a Fluidic System to Support Facile Target Enrichment and Washing Prior to Amplification and Detection To incorporate the lateral flow capture and buffer exchange systems into a compact and self-contained housing, a supporting fluidic system was devised. The fluidic system was fabricated to accommodate a nitrocellulose or chromatography paper buffer exchanger such as that shown in FIG. 14A by cutting polycarbonate sheet using a laser cutter into the geometries shown in FIG. 14B-D. Appropriately cut polycarbonate sheet was laminated to form sample and buffer wells using UV cured adhesive or water proof double-sided tape (ACE double-sided carpet tape 50106). The resulting devices allowed sample and wash buffers to be introduced at the time of assay initiation and supported sample chromatography and washing without further user intervention.

Example 9

Isolation of Citrus Tristeza Virus RNA from Citrus Leaf and Petiole Tissue

Figure 17:
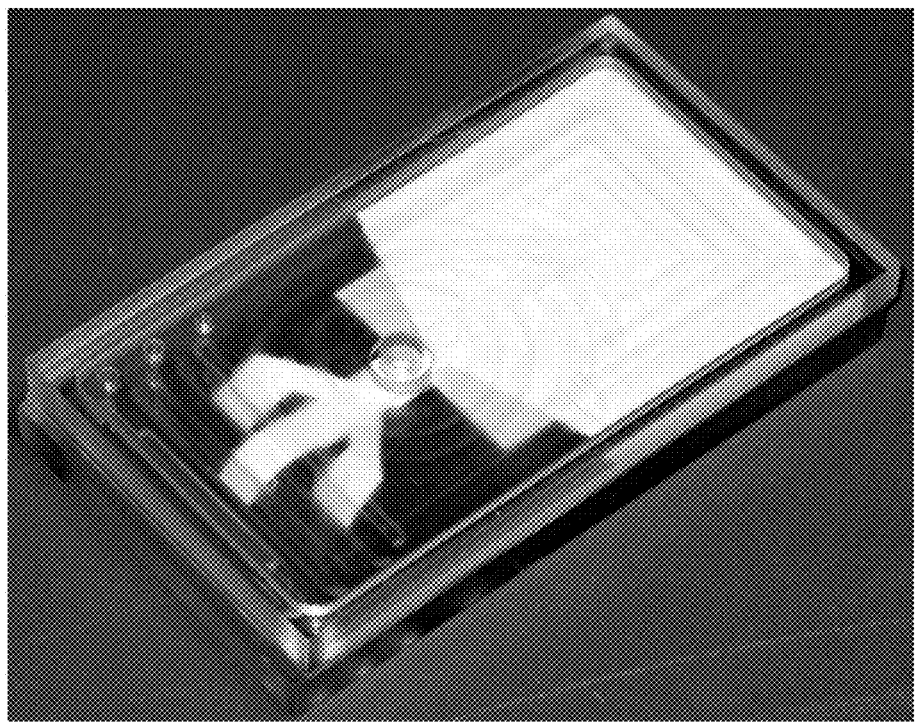
FIG. 17. A passive buffer exchange device for processing 100-200 µL of sample using up to 250 µL of a first wash buffer and up to 400 µL of a second wash buffer. The length and width of the device is similar to that of a credit card (55 mm×90 mm). The thickness of the device is 8 mm.
Figure 18:
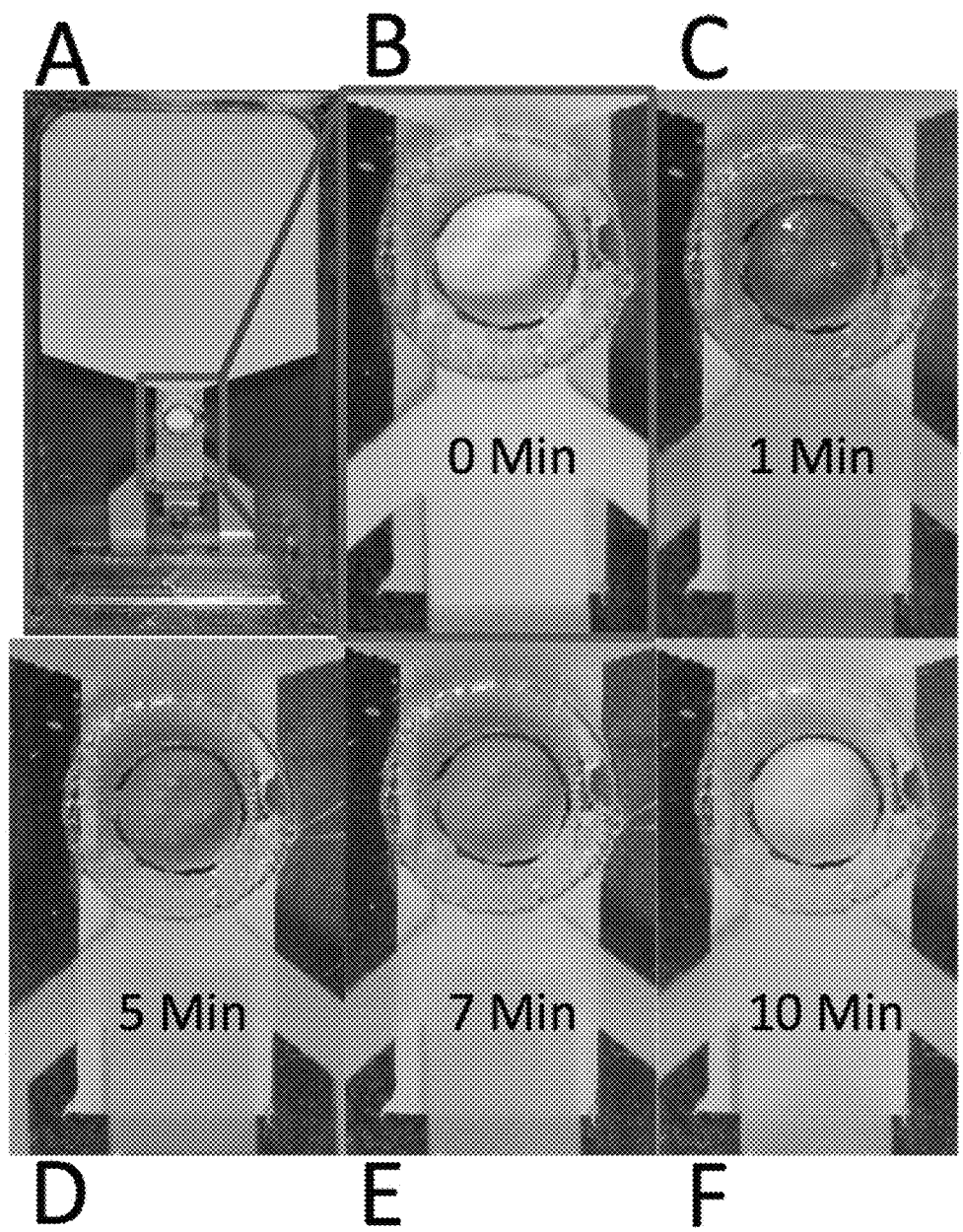
FIG. 18. (A) A credit card sized passive buffer exchange sample preparation device was used to process crude citrus leaf and petiole extract. (B) The sample input region of the device depicted in part A following the addition of wash buffers and prior to the addition of sample. (C) The sample input region of the device one minute after the addition of citrus tissue extract. A dark green discoloration of the glass fiber nucleic acid binding matrix is visible. (D) The sample input region of the device five minutes after the addition of citrus tissue extract. The green discoloration of the glass fiber nucleic acid binding material is limited to the upper portion of the material while the lower portion of the material displays a red discoloration indicative of migration of the first wash buffer into the nucleic acid binding material. (E) By seven minutes after the addition of sample the first wash buffer has replaced the green sample-derived discoloration generating a red color on the glass fiber pad. (F) By ten minutes the first wash buffer has been exhausted and the nucleic acid binding material is white indicating the removal of sample and wash buffer 1 solution by the second wash buffer.
Figure 19:
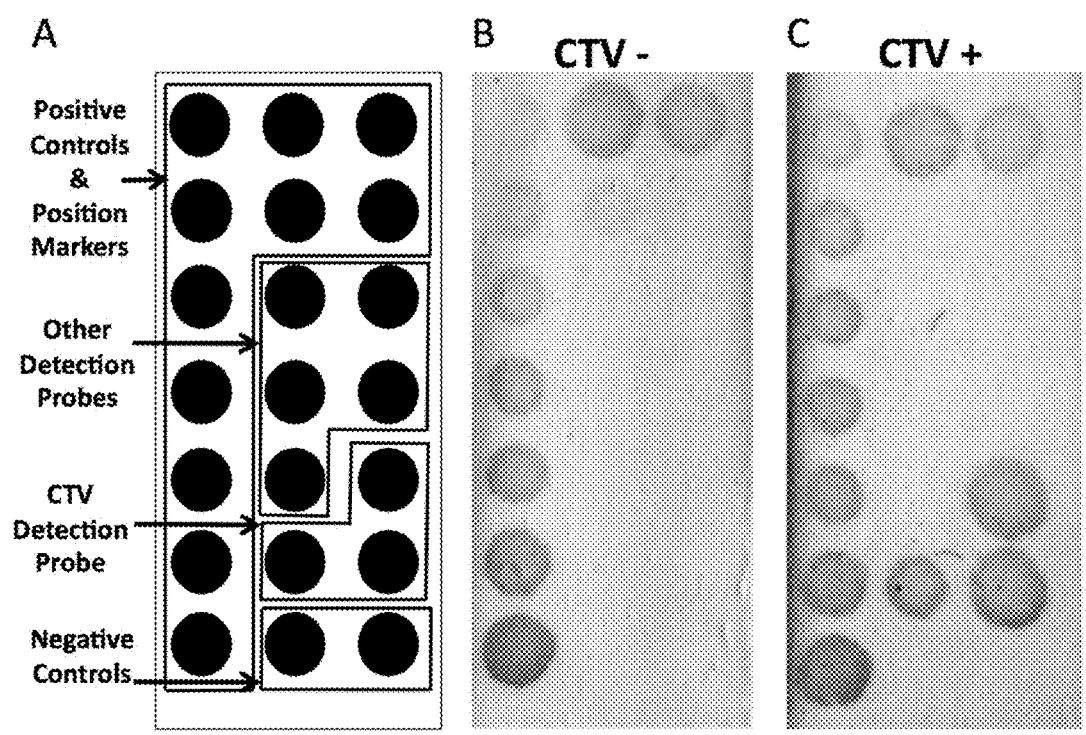
FIG. 19. A lateral flow microarray (LFM) was used to detect amplified CTV RNA from citrus tissue nucleic acids isolated using the passive sample preparation system. (A) is a schematic legend of the LFM layout. Positive controls confirm proper test performance and provide positional markers. Negative controls confirm assay specificity. The location of diagnostic probes for CTV and other targets are indicated. (B) One of twenty trees examined were negative for CTV by both the passive sample preparation method and Qiagen RNeasy, a laboratory-based approach. (C) A representative CTV positive LFM reveals strongly positive spots (blue) at corresponding CTV probe locations on the strip.

Passive buffer exchange structures were cut from backed nitrocellulose (Millipore, HiFlow HF-90) in lateral flow contact with a nucleic acid affinity binding matrix (GF/B glass fiber filter, Whatman) in turn placed in contact with an absorbent pad comprised of chromatography paper (3 MM, Whatman). The absorbent components were assembled in a housing fabricated from acrylic sheet plastic cut to provide sample and wash buffer reservoirs using a laser cutter (FIG. 17). Wash buffers were added, prior to sample addition, to corresponding device reservoirs. Sample consisting of 4 biopsy punches (1.5 mm punch) of citrus leaf and petiole tissue was ground in lysis buffer (100 μL of 4M guanidinium thiocyanate, 30% ethanol, 1% beta-mercaptoethanol, 25 mM sodium citrate pH 6.4) and the resulting extract introduced directly to the device (FIG. 18). Following completion of capillary flow of sample and wash buffers (Wash 1: 50 μL of 2M guanidinium thiocyanate, 30% ethanol, 25 mM Tris pH 7.4; Wash 2: 300 μL of 400 mM NaCl, 10 mM Tris pH 6.8) the glass fiber filter material was collected from the device by punching the filter material through an underlying hole and into a chamber where nucleic acids were eluted in 50 μL of H2O. The first wash buffer contained a red dye to allow visualization of buffer flow and replacement. Collected nucleic acids were assayed for citrus tristeza virus (CTV) by NASBA amplification followed by colorimetric detection on lateral flow microarrays (FIG. 19).

LFM detection of CTV amplicons made use of capture probe CTV-CAP immobilized on the LFM substrate:

```
CTV-CAP:
                                        [SEQ ID NO: 4]
    5'-CTGATTTAGAATGTGCTGTG-3'
``` and a detection probe:

```
UNI-det-5Tbio:
                                        [SEQ ID NO: 7]
    5'-TT-U-biotin-TTTT-U-biotin-TTTT-U-biotin- TTTTTTT gat gca agg tcg cat atg ag-3'
``` visualized by streptavidin conjugated dyed polystyrene microsphere (Spherotech) capture.

NASBA amplification of CTV diagnostic sequence was accomplished using:

```
CTV-P1:
                                        [SEQ ID NO: 10]
5'-aat tct aat acg act cac tat agg g aga T TTT
CAA CAA TTG TTC TTT A-3'
and CTV-P2:
                                        [SEQ ID NO: 11]
5'-gat gca agg tcg cat atg ag TTT GAG TTA TGG CGG
ACG TC-3'
```

The CTV-P2 primer incorporates a tag sequence into the NASBA product that is capable of hybridizing to the UNI-det-5Tbio oligonucleotide to mediate detection.

Positive controls and position markers printed on the LFM consisted of UNI-det-5Tbio which produces a colorimetric signal resulting from direct binding of the streptavidin conjugated dyed polystyrene microspheres to the biotin moieties on this oligonucleotide.

Example 10

Isolation of RNA from Human Whole Blood

Figure 20:
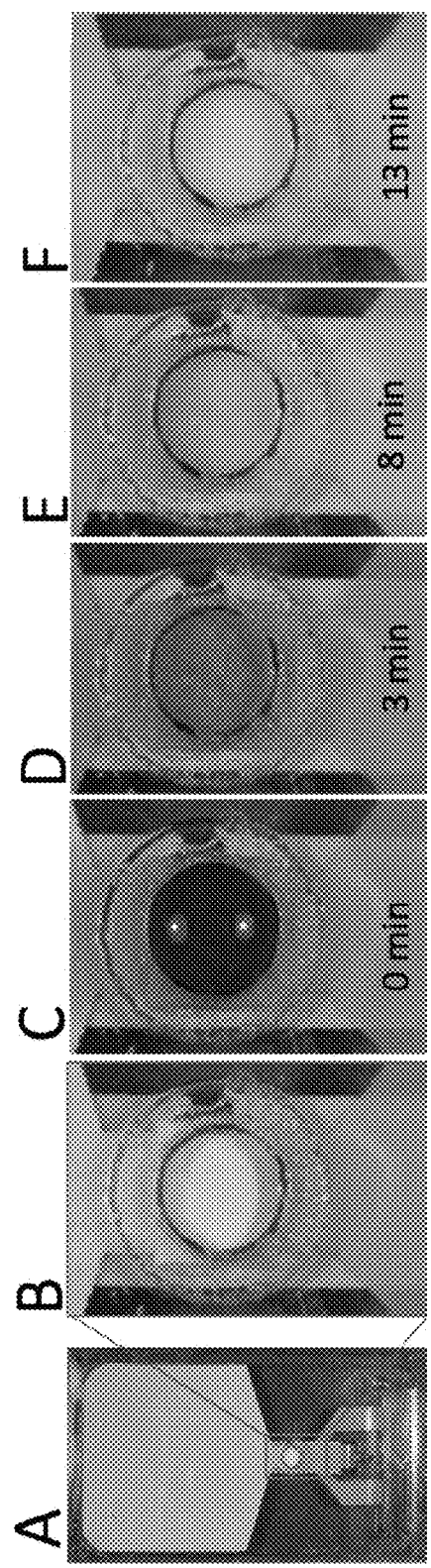
FIG. 20. (A) Top view of the passive buffer exchange sample preparation device immediately following the addition of the first and second wash buffers. The first wash buffer is doped with a red dye to facilitate visualization of buffer exchange progress. (B) Close-up view of the sample input well in the wash buffer primed device. (C) The device sample port immediately following the addition of whole blood in lysis buffer (t=0 minutes). (D) After 3 minutes the crude blood lysate has been transported through the glass fiber nucleic acid affinity matrix underlying the sample well. A brown discoloration, resulting from residual blood lysate within the affinity matrix, is visible. (E) 8 minutes after sample addition, the first wash buffer has washed residual blood lysate from the affinity matrix. A light red discoloration, resulting from the red dye in the first wash buffer, is visible. (F) 13 minutes after sample addition the second wash buffer has cleared the affinity matrix of the first wash buffer. A white affinity matrix is seen in the bottom of the sample well. Nucleic acids were collected by punching the glass fiber filter into an underlying elution chamber containing 50 µL of H2O.

A synthetic RNA template derived from the phi X 174 bacteriophage genome was generated by in vitro transcription. The resulting transcript was quantified spectrophotometrically and 20,000 copies were added to H2O or human whole blood lysate to generate test sample for processing with the lateral flow sample preparation device. 100 µL sample lysate consisting of 5 µL H2O or whole blood, in 95 µL 4M guanidinium thiocyanate, 1% beta-mercaptoethanol, 25 mM sodium citrate pH 6.4, and 30% ethanol were introduced to the sample input port immediately following the introduction of two wash buffers to the wash buffer reservoirs (Wash 1: 50 µL of 2M guanidinium thiocyanate, 30% ethanol, 25 mM Tris pH 7.5; Wash 2: 300 µL of 50 mM MOPS, pH 7.0, 1.5M NaCl, 0.15% Triton X-100, 30% ethanol). The first wash buffer contained a red dye to allow visualization of buffer flow and replacement. FIG. 20 depicts the device during the processing of whole blood lysate. Following the completion of buffer flow, nucleic acids were harvested from the device by inserting a 1 cc syringe without needle into the sample well and punching the glass fiber filter into an underlying chamber containing 50 µL of H2O to accomplish the elution of nucleic acids from the filter. The liberated nucleic acids were subjected to real-time NASBA detection using NASBA primers

```
Phix174-P2:
                                      [SEQ ID NO: 12]
GAT GCA AGG TCG CAT ATG AG T TAT GGT GAA CAG TGG
ATT A
and Phix174-P1:
                                      [SEQ ID NO: 13]
AAT TCT AAT ACG ACT CAC TAT AGG GGA AAC AAA TGC
TTA GGG ATT
```

Real-time NASBA detection was accomplished using a molecular beacon:

```
Phix174-beacon:
                                      [SEQ ID NO: 14]
5'-/56-FAM/CATAACGATACCAC/ideoxyU/GACCC/ideoxyU/

C/3BHQ_1/-3'
```

Figure 21:
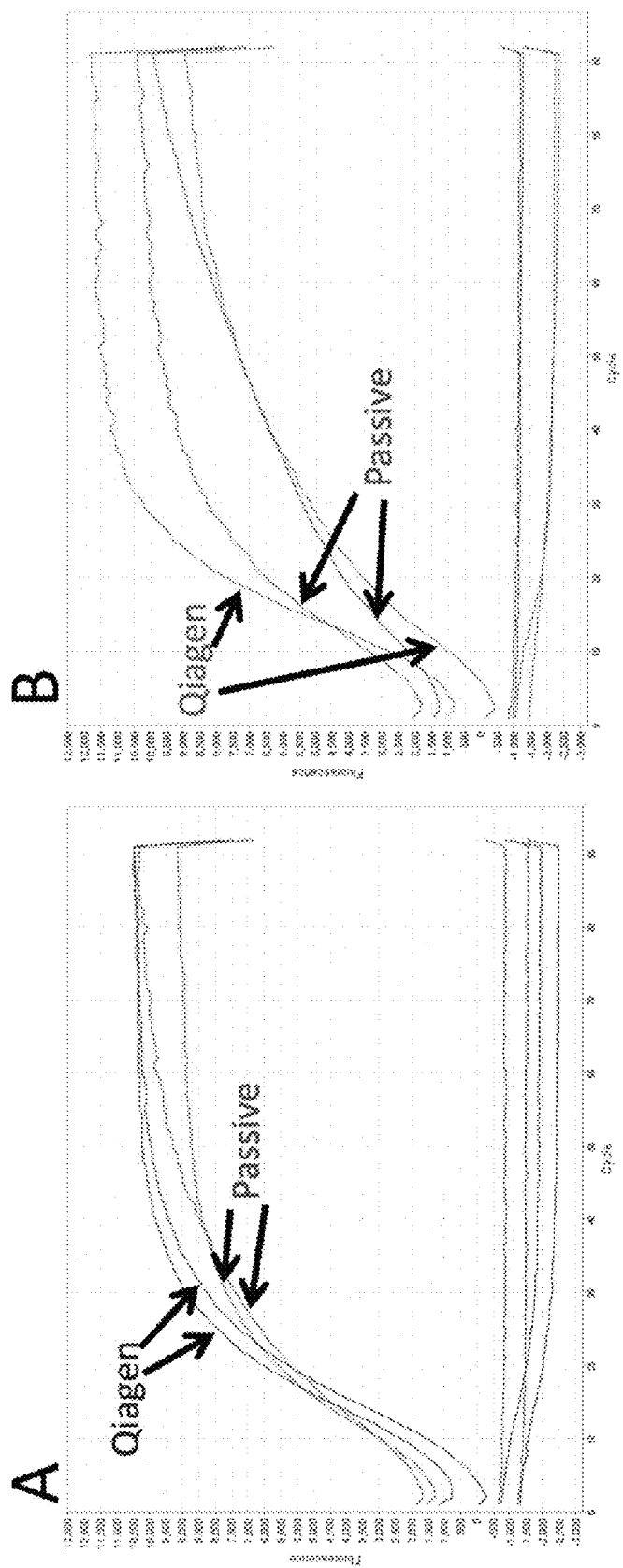
FIG. 21. Comparative study of passive buffer exchange mediated nucleic acid isolation from human whole blood with Qiagen RNeasy spin columns. Tests made use of an in vitro synthesized transcript derived from the phi X 174 bacteriophage genome. (A) Water spiked with 20,000 copies of an RNA generated by in vitro transcription was processed using Qiagen RNeasy spin columns and associated buffers (Qiagen, blue) or by passive buffer exchange device (Passive, red). Real-time NASBA amplification using a molecular beacon for detection provided similar results for both passive and Qiagen methods. (B) Human whole blood lysates spiked with the same amplicon as in part A was processed by Qiagen RNeasy or the passive buffer exchange system. Two representative blood samples are depicted here. Both Qiagen and the passive RNA isolation procedures yielded RNA suitable for real-time NASBA amplification with similar efficiency.

These studies show that the device and associated buffers provide target nucleic acid isolation efficiency similar to that afforded by commercial spin column systems, e.g. Qiagen RNeasy (FIG. 21).

Example 11

Isolation of Influenza Viral RNA from Human Nasal Swab Samples

Passive buffer exchange sample preparation was employed for the isolation of RNA from anonymous patient samples positive for influenza A by QUIDEL QuickVue immunoassays. 100 µL sample lysate consisting of nasal swab sample, 2M guanidinium thiocyanate, 30% ethanol, 25 mM sodium citrate pH 6.4 were introduced to the sample port immediately following the introduction of two wash buffers to the wash buffer reservoirs (Wash 1: 50 µL of 2M guanidinium thiocyanate, 30% ethanol, 25 mM Tris pH 7.4; Wash 2: 300 µL of 400 mM NaCl, 10 mM Tris pH 6.8). The first wash buffer contained a red dye to allow visualization of buffer flow and replacement. Collected nucleic acids were subjected to real-time reverse transcriptase PCR using the Center for Disease Control's (CDC) influenza A assays. As a control the same samples were processed in parallel using Qiagen RNeasy spin columns and the resulting RNA subject to identical CDC influenza A diagnostic assays. Table 1 summarizes the results. NTC is a no template negative control.

TABLE 1

| Sample | Passive buffer exchange | RNeasy (Qiagen) | QuickVue |
|--------|------------------------|-----------------|----------|
| 1 | + | + | + |
| 2 | + | + | + |
| 3 | + | + | + |
| 4 | + | + | + |
| 5 | + | + | + |
| NTC | − | − | ND |

The present invention is not to be limited in scope by the embodiments disclosed herein, which are intended as single illustrations of individual aspects of the invention, and any which are functionally equivalent are within the scope of the invention. Various modifications to the models and methods of the invention, in addition to those described herein, will become apparent to those skilled in the art from the foregoing description and teachings, and are similarly intended to fall within the scope of the Invention. Such modifications or other embodiments can be practiced without departing from the true scope and spirit of the invention. The entire disclosures of all references, applications, patents, and publications cited above are hereby incorporated by reference as if each individual publication or patent application were specifically and individually indicated to be incorporated by reference.

What is claimed is:

1. A device for processing a sample comprising a material which defines a flow path and which comprises the following elements:
- a sample receiving zone for receiving an aliquot of a fluid sample which comprises targets comprising nucleic acids;
- a capture zone in capillary flow contact with said sample receiving zone for binding and/or purifying the targets;
- a capillary flow path comprising said material and connecting said sample receiving zone and said capture zone; and
- one or more assay zones, each assay zone connected to said capillary flow path via two solution flow paths comprising said material, each said solution flow path forming a junction with said capillary flow path downstream of said sample receiving zone; each said solution flow path configured to deliver a corresponding solution to said capillary flow path or said capture zone at a desired time or sequence after the aliquot and each solution are all added to the device at the time of assay initiation;
- wherein for each assay zone said two junctions are on opposite sides of said capillary flow path; and
- wherein the material comprises an absorbent material capable of supporting fluid wicking and the passive control of at least one fluid flow therein.

2. The device according to claim 1, further comprising a lysis zone, in capillary flow contact with said capture zone, which is capable of achieving the lysis of the membrane(s) of a biological particle or cell comprising one or more targets and the liberation of nucleic acid therefrom.

3. The device according to claim 2, wherein the lysis zone comprises a microporous membrane.

4. The device according to claim 3, wherein the microporous membrane comprises nitrocellulose.

5. The device according to claim 2, wherein the lysis zone comprises an absorbent material capable of supporting fluid wicking and the passive control of at least one fluid flow therein.

6. The device according to claim 5 wherein the absorbent material comprises nitrocellulose.

7. The device according to claim 1, wherein said assay zones comprise the nucleic acid and labeling constituents for a sandwich nucleic acid hybridization assay.

8. The device according to claim 1, further comprising a nucleic acid amplification zone downstream of and in capillary flow contact with the capture zone, and upstream and in capillary flow contact with said one or more assay zones.

9. The device according to claim 1, wherein the capture zone comprises a microporous membrane.

10. The device according to claim 9, wherein the microporous membrane comprises nitrocellulose.

11. The device according to claim 1, wherein one or more of the assay zones comprises a microporous membrane.

12. The device according to claim 11, wherein the microporous membrane comprises nitrocellulose.

13. The device according to claim 1, wherein the sample receiving zone and/or capture zone comprises an absorbent material capable of supporting fluid wicking and the passive control of at least one fluid flow therein.

14. The device according to claim 13 wherein the absorbent material comprises nitrocellulose.

15. The device according to claim 1, wherein said capture zone comprises immobilized ligands for binding the targets, silica, glass fiber, and/or diethyl aminoethyl (DEAE) membrane.

16. The device according to claim 1, wherein the absorbent material allows for the passive control of multiple fluid flows therein.

17. The device according to claim 1 wherein the absorbent material comprises nitrocellulose.

* * * * *

UNITED STATES PATENT AND TRADEMARK OFFICE
CERTIFICATE OF CORRECTION

| | | |
|---|---|---|
| PATENT NO. | : 9,207,236 B2 | Page 1 of 1 |
| APPLICATION NO. | : 12/940973 | |
| DATED | : December 8, 2015 | |
| INVENTOR(S) | : Cary | |

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 822 days.

Signed and Sealed this
Twenty-third Day of August, 2016

Michelle K. Lee
*Director of the United States Patent and Trademark Office*